US011519913B2

United States Patent
Yates et al.

(10) Patent No.: US 11,519,913 B2
(45) Date of Patent: Dec. 6, 2022

(54) METABOLIC DISORDER TARGET

(71) Applicant: University of Pittsburgh—Of the Commonwealth System of Higher Education, Pittsburgh, PA (US)

(72) Inventors: Nathan A. Yates, Piscataway, NJ (US); Steven James Mullett, McMurray, PA (US); Harris B. Bell-Temin, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1030 days.

(21) Appl. No.: 16/309,056

(22) PCT Filed: Jun. 21, 2017

(86) PCT No.: PCT/US2017/038461
§ 371 (c)(1),
(2) Date: Dec. 11, 2018

(87) PCT Pub. No.: WO2017/223156
PCT Pub. Date: Dec. 28, 2017

(65) Prior Publication Data
US 2019/0310254 A1 Oct. 10, 2019

Related U.S. Application Data

(60) Provisional application No. 62/353,526, filed on Jun. 22, 2016.

(51) Int. Cl.
*A61P 3/10* (2006.01)
*G01N 33/573* (2006.01)
*G01N 30/72* (2006.01)

(52) U.S. Cl.
CPC ............. *G01N 33/573* (2013.01); *A61P 3/10* (2018.01); *G01N 30/72* (2013.01); *G01N 2333/90216* (2013.01)

(58) Field of Classification Search
None
See application file for complete search history.

(56) References Cited

PUBLICATIONS

Drahota et al. "Biguanides inhibit complex I, II and IV of rat liver mitochondria and modify their functional properties." *Physiological Research* vol. 63, No. 1 (2014): pp. 1-11.
Ferrannini. "The target of metformin in type 2 diabetes." *New England Journal of Medicine* vol. 371, No. 16 (2014): pp. 1547-1548.
International Search Report and Written Opinion for PCT/US2017/038461, dated Sep. 17, 2017, by the Israel Patent Office acting as ISA (8 pages).
Jafari et al. "The cellular thermal shift assay for evaluating drug target interactions in cells." *Nature Protocols* vol. 9, No. 9 (2014): pp. 2100-2122.
Kim et al. "Metformin prevents fatty liver and improves balance of white/brown adipose in an obesity mouse model by inducing FGF21." *Mediators of Inflammation* vol. 2016 (2016): pp. 1-13.
Molina et al. "Monitoring drug target engagement in cells and tissues using the cellular thermal shift assay." *Science* vol. 341, No. 6141 (2013): pp. 84-87.
Pai et al. "Drug affinity responsive target stability (DARTS) for small-molecule target identification." *Methods in Molecular Biology* vol. 1263 (2015): pp. 287-298.
Protti et al. "Metformin overdose causes platelet mitochondrial dysfunction in humans." *Critical Care* vol. 16, No. 5 (2012): pp. R180.
Whitaker-Menezes et al. "Hyperactivation of oxidative mitochondrial metabolism in epithelial cancer cells in situ: visualizing the therapeutic effects of metformin in tumor tissue." *Cell Cycle* vol. 10, No. 23 (2011): pp. 4047-4064.

*Primary Examiner* — Christopher M Gross
(74) *Attorney, Agent, or Firm* — Klarquist Sparkman, LLP

(57) ABSTRACT

Methods are disclosed herein for identifying a compound of use in treating a condition treatable by metformin. The methods include determining if the test compound binds a subunit of the mitochondrial electron transport complex IV, and/or alters the function of the mitochondrial electron transport complex IV. Methods for treating a subject with a condition treatable by metformin, are also disclosed. In some embodiments, the condition is type II diabetes.

11 Claims, 5 Drawing Sheets

Specification includes a Sequence Listing.

FIG. 1
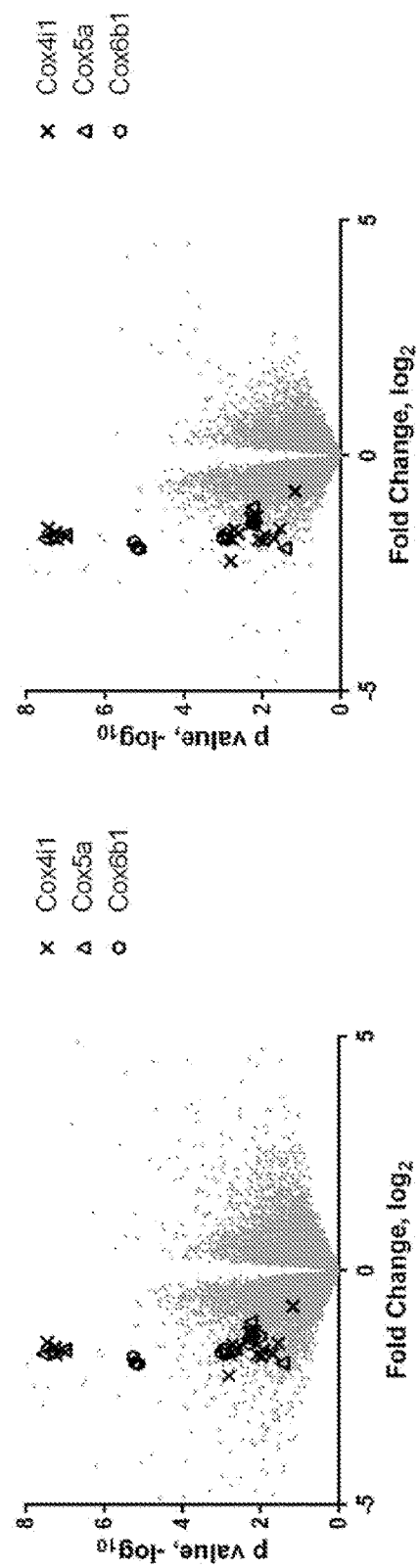
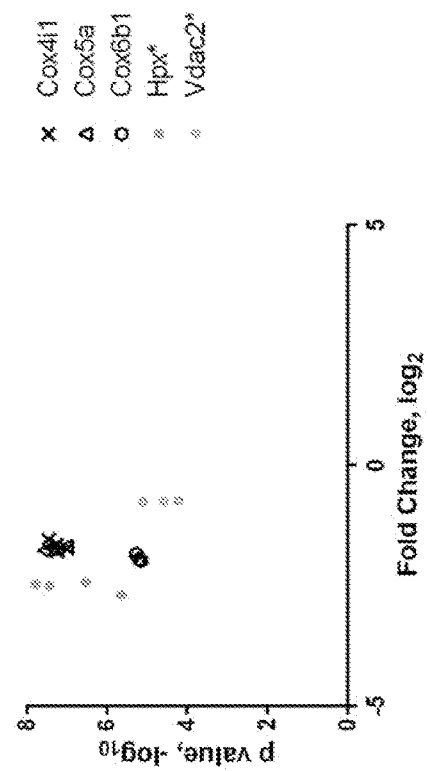
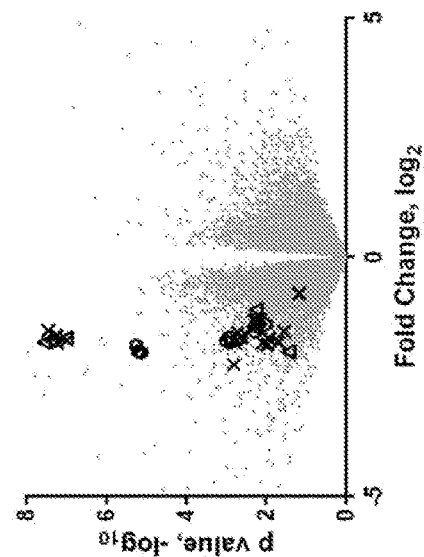
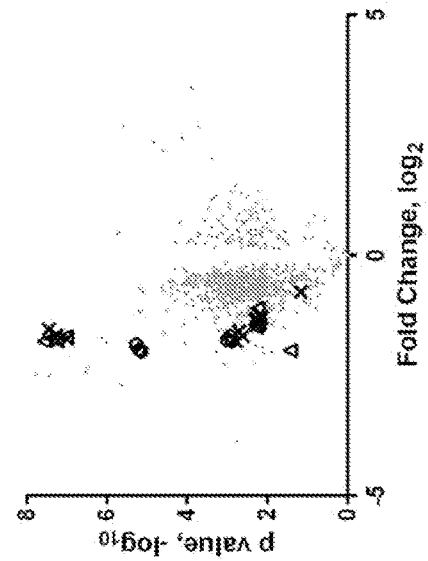

FIG. 2

COX4I1, COX5A, COX6B

- 10 of the top 17 features draw from the three members of complex IV

Cytochrome C Oxidase Subunit IV, Isoform 1, 4 peptides (1 oxidized alternate)
SEQ ID NO: 10
MLASRALSLI GKRAISTSVC LRAHGSVVKS EDYAFPTYAD RRDYPLPDVA HVTMLSASQK ALKEKEKADW SSLSRDEKVQ LYRIQFNESF
AEMNRGTNEW KTVVGMAMFF IGFTALVLIW EKSYVYGPIP HTFDRDWVAM QTKRMLDMKA NPIQGFSAKW DYDKNEWKK Cytochrome C Oxidase Subunit 5A, 2 peptides
SEQ ID NO: 11
MLAAALRRCT AAAAARGLLH PASAPSPAAA VCSIRCYSHG SHETDEEFDA RWVTYFNKPD IDAWELRKGM NTLVGYDLVP EPKIIDAALR
ACRRLNDFAS AVRILEVVKD KAGPHKEIYP YVIQELRPTL NELGISTPEE LGLDKV Cytochrome C Oxidase Subunit 6B, 3 peptides
SEQ ID NO: 12
MAEDIKTKIK NYKTAPFDSR FPNQNQTKNC WQNYLDFHRC EKAMTAKGGD VSVCEWYRRV YKSLCPVSWV SAWDDRIAEG TFPGKI

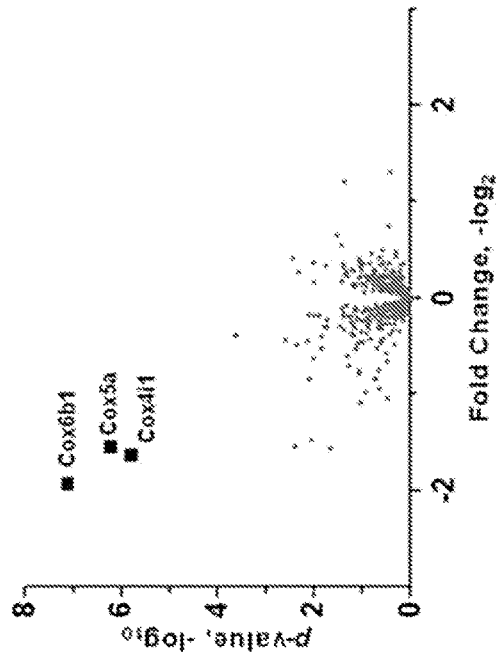
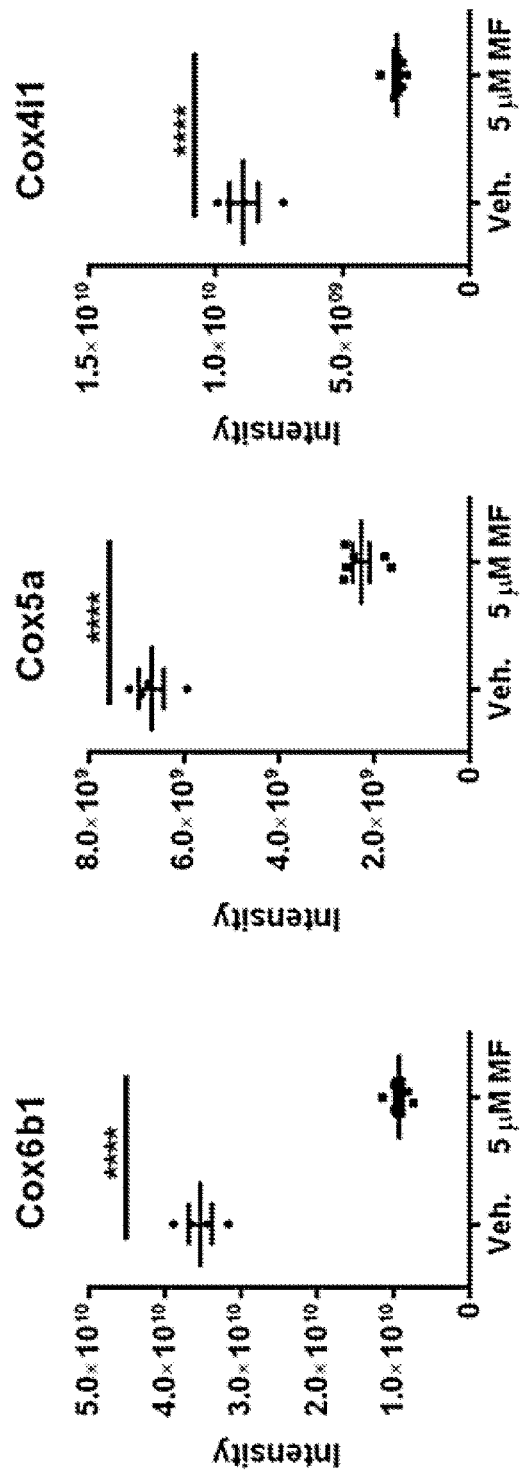
FIG. 3

SEQUENCE LISTING

<160> NUMBER OF SEQ ID NOS: 12

<210> SEQ ID NO 1
<211> LENGTH: 169
<212> TYPE: PRT
<213> ORGANISM: Homo sapiens

<400> SEQUENCE: 1

Met Leu Ala Thr Arg Val Phe Ser Leu Val Gly Lys Arg Ala Ile Ser
1               5                   10                  15

Thr Ser Val Cys Val Arg Ala His Glu Ser Val Val Lys Ser Glu Asp
            20                  25                  30

Phe Ser Leu Pro Ala Tyr Met Asp Arg Arg Asp His Pro Leu Pro Glu
        35                  40                  45

Val Ala His Val Lys His Leu Ser Ala Ser Gln Lys Ala Leu Lys Glu
    50                  55                  60

Lys Glu Lys Ala Ser Trp Ser Ser Leu Ser Met Asp Glu Lys Val Glu
65                  70                  75                  80

Leu Tyr Arg Ile Lys Phe Lys Glu Ser Phe Ala Glu Met Asn Arg Gly
                85                  90                  95

Ser Asn Glu Trp Lys Thr Val Val Gly Gly Ala Met Phe Phe Ile Gly
            100                 105                 110

Phe Thr Ala Leu Val Ile Met Trp Gln Lys His Tyr Val Tyr Gly Pro
        115                 120                 125

Leu Pro Gln Ser Phe Asp Lys Glu Trp Val Ala Lys Gln Thr Lys Arg
    130                 135                 140

Met Leu Asp Met Lys Val Asn Pro Ile Gln Gly Leu Ala Ser Lys Trp
145                 150                 155                 160

Asp Tyr Glu Lys Asn Glu Trp Lys Lys
                165

<210> SEQ ID NO 2
<211> LENGTH: 150
<212> TYPE: PRT
<213> ORGANISM: Homo sapiens

<400> SEQUENCE: 2

Met Leu Gly Ala Ala Leu Arg Arg Cys Ala Val Ala Ala Thr Thr Arg
1               5                   10                  15

Ala Asp Pro Arg Gly Leu Leu His Ser Ala Arg Thr Pro Gly Pro Ala
            20                  25                  30

Val Ala Ile Gln Ser Val Arg Cys Tyr Ser His Gly Ser Gln Glu Thr
        35                  40                  45

Asp Glu Glu Phe Asp Ala Arg Trp Val Thr Tyr Phe Asn Lys Pro Asp
    50                  55                  60

Ile Asp Ala Trp Glu Leu Arg Lys Gly Ile Asn Thr Leu Val Thr Tyr
65                  70                  75                  80

Asp Met Val Pro Glu Pro Lys Ile Ile Asp Ala Ala Leu Arg Ala Cys
                85                  90                  95

Arg Arg Leu Asn Asp Phe Ala Ser Thr Val Arg Ile Leu Glu Val Val
            100                 105                 110

Lys Asp Lys Ala Gly Pro His Lys Glu Ile Tyr Pro Tyr Val Ile Gln
        115                 120                 125

Glu Leu Arg Pro Thr Leu Asn Glu Leu Gly Ile Ser Thr Pro Glu Glu
    130                 135                 140

Leu Gly Leu Asp Lys Val

-continued

<210> SEQ ID NO 3
<211> LENGTH: 109
<212> TYPE: PRT
<213> ORGANISM: Homo sapiens

<400> SEQUENCE: 3

```
Met Ala Val Val Gly Val Ser Ser Val Ser Arg Leu Leu Gly Arg Ser
1               5                   10                  15

Arg Pro Gln Leu Gly Arg Pro Met Ser Ser Gly Ala His Gly Glu Glu
                20                  25                  30

Gly Ser Ala Arg Met Trp Lys Thr Leu Thr Phe Phe Val Ala Leu Pro
            35                  40                  45

Gly Val Ala Val Ser Met Leu Asn Val Tyr Leu Lys Ser His His Gly
        50                  55                  60

Glu His Glu Arg Pro Glu Phe Ile Ala Tyr Pro His Leu Arg Ile Arg
65                  70                  75                  80

Thr Lys Pro Phe Pro Trp Gly Asp Gly Asn His Thr Leu Phe His Asn
                85                  90                  95

Pro His Val Asn Pro Leu Pro Thr Gly Tyr Glu Asp Glu
                100                 105
```

<210> SEQ ID NO 4
<211> LENGTH: 115
<212> TYPE: PRT
<213> ORGANISM: Homo sapiens

<400> SEQUENCE: 4

```
Met His Thr Gln Asp Ser Glu Val Val Pro Val Pro Ala Trp Pro Phe
1               5                   10                  15

Ser Leu Val Val Phe Ser Cys Gly Gly Cys Trp Ser Val Thr Ala Lys
                20                  25                  30

Met Leu Arg Asn Leu Leu Ala Leu Arg Gln Ile Gly Gln Arg Thr Ile
            35                  40                  45

Ser Thr Ala Ser Arg Arg His Phe Lys Asn Lys Val Pro Glu Lys Gln
        50                  55                  60

Lys Leu Phe Gln Glu Asp Asp Glu Ile Pro Leu Tyr Leu Lys Gly Gly
65                  70                  75                  80

Val Ala Asp Ala Leu Leu Tyr Arg Ala Thr Met Ile Leu Thr Val Gly
                85                  90                  95

Gly Thr Ala Tyr Ala Ile Tyr Gly Leu Ala Val Ala Ser Phe Pro Lys
                100                 105                 110

Lys Gln Glu
        115
```

<210> SEQ ID NO 5
<211> LENGTH: 227
<212> TYPE: PRT
<213> ORGANISM: Homo sapiens

<400> SEQUENCE: 5

```
Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
                20                  25                  30

Leu Ile Cys Phe Leu Val Leu Tyr Ala Leu Phe Leu Thr Leu Thr Thr
            35                  40                  45
```

```
Lys Leu Thr Asn Thr Asn Ile Ser Asp Ala Gln Glu Met Glu Thr Val
 50                  55                  60

Trp Thr Ile Leu Pro Ala Ile Ile Leu Val Leu Ile Ala Leu Pro Ser
 65                  70                  75                  80

Leu Arg Ile Leu Tyr Met Thr Asp Glu Val Asn Asp Pro Ser Leu Thr
                 85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
    130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205

Ile Val Leu Glu Leu Ile Pro Leu Lys Ile Phe Glu Met Gly Pro Val
210                 215                 220

Phe Thr Leu
225

<210> SEQ ID NO 6
<211> LENGTH: 75
<212> TYPE: PRT
<213> ORGANISM: Homo sapiens

<400> SEQUENCE: 6

Met Ala Pro Glu Val Leu Pro Lys Pro Arg Met Arg Gly Leu Leu Ala
 1               5                  10                  15

Arg Arg Leu Arg Asn His Met Ala Val Ala Phe Val Leu Ser Leu Gly
                 20                  25                  30

Val Ala Ala Leu Tyr Lys Phe Arg Val Ala Asp Gln Arg Lys Lys Ala
            35                  40                  45

Tyr Ala Asp Phe Tyr Arg Asn Tyr Asp Val Met Lys Asp Phe Glu Glu
        50                  55                  60

Met Arg Lys Ala Gly Ile Phe Gln Ser Val Lys
 65                  70                  75

<210> SEQ ID NO 7
<211> LENGTH: 63
<212> TYPE: PRT
<213> ORGANISM: Homo sapiens

<400> SEQUENCE: 7

Met Leu Gly Gln Ser Ile Arg Arg Phe Thr Thr Ser Val Val Arg Arg
 1               5                  10                  15

Ser His Tyr Glu Glu Gly Pro Gly Lys Asn Leu Pro Phe Ser Val Glu
                 20                  25                  30

Asn Lys Trp Ser Leu Leu Ala Lys Met Cys Leu Tyr Phe Gly Ser Ala
            35                  40                  45

Phe Ala Thr Pro Phe Leu Val Val Arg His Gln Leu Leu Lys Thr
        50                  55                  60
```

```
<210> SEQ ID NO 8
<211> LENGTH: 129
<212> TYPE: PRT
<213> ORGANISM: Homo sapiens

<400> SEQUENCE: 8

Met Ala Ser Arg Leu Leu Arg Gly Ala Gly Thr Leu Ala Ala Gln Ala
1               5                   10                  15

Leu Arg Ala Arg Gly Pro Ser Gly Ala Ala Met Arg Ser Met Ala
                20                  25                  30

Ser Gly Gly Gly Val Pro Thr Asp Glu Glu Gln Ala Thr Gly Leu Glu
            35                  40                  45

Arg Glu Ile Met Leu Ala Ala Lys Lys Gly Leu Asp Pro Tyr Asn Val
    50                  55                  60

Leu Ala Pro Lys Gly Ala Ser Gly Thr Arg Glu Asp Pro Asn Leu Val
65                  70                  75                  80

Pro Ser Ile Ser Asn Lys Arg Ile Val Gly Cys Ile Cys Glu Glu Asp
                85                  90                  95

Asn Thr Ser Val Val Trp Phe Trp Leu His Lys Gly Glu Ala Gln Arg
            100                 105                 110

Cys Pro Arg Cys Gly Ala His Tyr Lys Leu Val Pro Gln Gln Leu Ala
        115                 120                 125

His

<210> SEQ ID NO 9
<211> LENGTH: 109
<212> TYPE: PRT
<213> ORGANISM: Homo sapiens

<400> SEQUENCE: 9

Met Ala Val Val Gly Val Ser Ser Val Ser Arg Leu Leu Gly Arg Ser
1               5                   10                  15

Arg Pro Gln Leu Gly Arg Pro Met Ser Ser Gly Ala His Gly Glu Glu
                20                  25                  30

Gly Ser Ala Arg Met Trp Lys Thr Leu Thr Phe Phe Val Ala Leu Pro
            35                  40                  45

Gly Val Ala Val Ser Met Leu Asn Val Tyr Leu Lys Ser His His Gly
    50                  55                  60

Glu His Glu Arg Pro Glu Phe Ile Ala Tyr Pro His Leu Arg Ile Arg
65                  70                  75                  80

Thr Lys Pro Phe Pro Trp Gly Asp Gly Asn His Thr Leu Phe His Asn
                85                  90                  95

Pro His Val Asn Pro Leu Pro Thr Gly Tyr Glu Asp Glu
            100                 105

<210> SEQ ID NO 10
<211> LENGTH: 169
<212> TYPE: PRT
<213> ORGANISM: Mus musculus

<400> SEQUENCE: 10

Met Leu Ala Ser Arg Ala Leu Ser Leu Ile Gly Lys Arg Ala Ile Ser
1               5                   10                  15

Thr Ser Val Cys Leu Arg Ala His Gly Ser Val Val Lys Ser Glu Asp
                20                  25                  30

Tyr Ala Phe Pro Thr Tyr Ala Asp Arg Arg Asp Tyr Pro Leu Pro Asp
```

```
                35                  40                  45
Val Ala His Val Thr Met Leu Ser Ala Ser Gln Lys Ala Leu Lys Glu
 50                  55                  60

Lys Glu Lys Ala Asp Trp Ser Ser Leu Ser Arg Asp Glu Lys Val Gln
 65                  70                  75                  80

Leu Tyr Arg Ile Gln Phe Asn Glu Ser Phe Ala Glu Met Asn Arg Gly
                 85                  90                  95

Thr Asn Glu Trp Lys Thr Val Val Gly Met Ala Met Phe Phe Ile Gly
                100                 105                 110

Phe Thr Ala Leu Val Leu Ile Trp Glu Lys Ser Tyr Val Tyr Gly Pro
                115                 120                 125

Ile Pro His Thr Phe Asp Arg Asp Trp Val Ala Met Gln Thr Lys Arg
                130                 135                 140

Met Leu Asp Met Lys Ala Asn Pro Ile Gln Gly Phe Ser Ala Lys Trp
145                 150                 155                 160

Asp Tyr Asp Lys Asn Glu Trp Lys Lys
                165

<210> SEQ ID NO 11
<211> LENGTH: 146
<212> TYPE: PRT
<213> ORGANISM: Mus musculus

<400> SEQUENCE: 11

Met Leu Ala Ala Ala Leu Arg Arg Cys Thr Ala Ala Ala Ala Ala Arg
 1                5                  10                  15

Gly Leu Leu His Pro Ala Ser Ala Pro Ser Pro Ala Ala Ala Val Cys
                 20                  25                  30

Ser Ile Arg Cys Tyr Ser His Gly Ser His Glu Thr Asp Glu Glu Phe
                 35                  40                  45

Asp Ala Arg Trp Val Thr Tyr Phe Asn Lys Pro Asp Ile Asp Ala Trp
 50                  55                  60

Glu Leu Arg Lys Gly Met Asn Thr Leu Val Gly Tyr Asp Leu Val Pro
 65                  70                  75                  80

Glu Pro Lys Ile Ile Asp Ala Ala Leu Arg Ala Cys Arg Arg Leu Asn
                 85                  90                  95

Asp Phe Ala Ser Ala Val Arg Ile Leu Glu Val Val Lys Asp Lys Ala
                100                 105                 110

Gly Pro His Lys Glu Ile Tyr Pro Tyr Val Ile Gln Glu Leu Arg Pro
                115                 120                 125

Thr Leu Asn Glu Leu Gly Ile Ser Thr Pro Glu Glu Leu Gly Leu Asp
                130                 135                 140

Lys Val
145

<210> SEQ ID NO 12
<211> LENGTH: 86
<212> TYPE: PRT
<213> ORGANISM: Mus musculus

<400> SEQUENCE: 12

Met Ala Glu Asp Ile Lys Thr Lys Ile Lys Asn Tyr Lys Thr Ala Pro
 1                5                  10                  15

Phe Asp Ser Arg Phe Pro Asn Gln Asn Gln Thr Lys Asn Cys Trp Gln
                 20                  25                  30

Asn Tyr Leu Asp Phe His Arg Cys Glu Lys Ala Met Thr Ala Lys Gly
```

```
                 35                  40                  45
Gly Asp Val Ser Val Cys Glu Trp Tyr Arg Arg Val Tyr Lys Ser Leu
    50                  55                  60

Cys Pro Val Ser Trp Val Ser Ala Trp Asp Asp Arg Ile Ala Glu Gly
65                  70                  75                  80

Thr Phe Pro Gly Lys Ile
                85
```

METABOLIC DISORDER TARGET

CROSS REFERENCE TO RELATED APPLICATIONS

This is the U.S. National Stage of International Application No. PCT/US2017/038461, filed Jun. 21, 2017, which was published in English under PCT Article 21(2), which in turn claims the benefit of U.S. Provisional Application No. 62/353,526, filed Jun. 22, 2016. The provisional application herein incorporated by reference in its entirety.

FIELD

This relates to methods for identifying agents of use in treating type II diabetes, and the use of agents identified by the method for treating diabetes.

BACKGROUND

Metformin (N,N-Dimethylimidodicarbonimidic diamide) is the first-line medication for the treatment of type 2 diabetes, and is also of use for the treatment of prediabetes cardiovascular disease, cancer, neurodegenerative conditions, and polycystic ovary syndrome. Metformin was discovered in 1922, and studies in humans began in 1950s. Use of this compound began the United States in 1995, and it is included on the World Health Organization's list of the most important medications needed in a basic health system. Metformin is believed to be the most widely used oral medication for type II diabetes. In addition, Metformin treatment of people at risk for type 2 diabetes may decrease their chances of developing the disease, although intensive physical exercise and dieting work significantly better for this purpose.

However, metformin is contraindicated in people with any condition that could increase the risk of lactic acidosis, including kidney disorders (defined as creatinine levels over 150 μmol/l (1.7 mg/dl)), lung disease and liver disease. Metformin has also been reported to decrease the blood levels of thyroid-stimulating hormone in people with hypothyroidism. In addition, lactic acidosis can occur in some patients. Thus, there is a need to identify other agents that can be used to treat type II diabetes.

SUMMARY

In some embodiments, methods are disclosed herein for identifying a compound of use in treating a condition treatable by metformin. The methods include contacting a sample comprising a mitochondrial electron transport complex IV with a test compound, and determining if the test compound binds a subunit of the mitochondrial electron transport complex IV, and/or alters the function of the mitochondrial electron transport complex IV. Binding of the test compound to a subunit of the mitochondrial electron transport complex IV, or change in function of the mitochondrial electron transport complex IV, indicates that the compound is of use in treating the condition. Compounds of use in treating a condition treatable by metformin, such as type II diabetes, are also disclosed.

In additional embodiments, methods are disclosed for treating a condition treatable by metformin in a subject, comprising the steps of: (a) identifying an agent that binds a subunit of the mitochondrial electron transport complex IV, and/or alters the function of the mitochondrial electron transport complex IV, and (b) treating the subject with the agent. In some non-limiting examples, the subject has type II diabetes.

In yet other embodiments, methods are disclosed for treating a condition in a subject, comprising administering to the subject an effective amount of a therapeutic agent that specifically binds a subunit of the mitochondrial electron transport complex IV wherein the agent is not metformin, thereby treating the condition in the subject. In some non-limiting examples, the subject has type II diabetes.

The foregoing and other objects, features, and advantages of the disclosure will become more apparent from the following detailed description, which proceeds with reference to the accompanying figures.

BRIEF DESCRIPTION OF THE DRAWINGS

FIG. 1: A volcano plots of metformin binding study. FIG. 1 shows the application of practical and statistical filters to reduce number the number of signals (36,000), to a manageable number for analysis, identifying three members of complex IV as very significant ($p<0.0001$).

FIG. 2: Coverage of members of Complex IV. FIG. 2 shows identified and quantified peptides (underlined) for three members of complex IV. Sequences shown in FIG. 2 are from *Mus musculus*: Cox4i1 is SEQ ID NO: 10, Cox5a is SEQ ID NO: 11, Cox6b is SEQ ID NO: 12.

FIG. 3: Differential solubilization of membrane proteins following 5 μM metformin treatment. Volcano plot with log transform of p-value on y-axis and negative log base 2 transform of fold change on the x axis. The three proteins identified as members of complex IV are labelled. Scattered dot plots for each protein is shown as mean and SEM and individual protein levels. Statistical analysis via Student's unpaired equal variance t-test. ****, $p<0.0001$.

SEQUENCE LISTING

Figure 4:
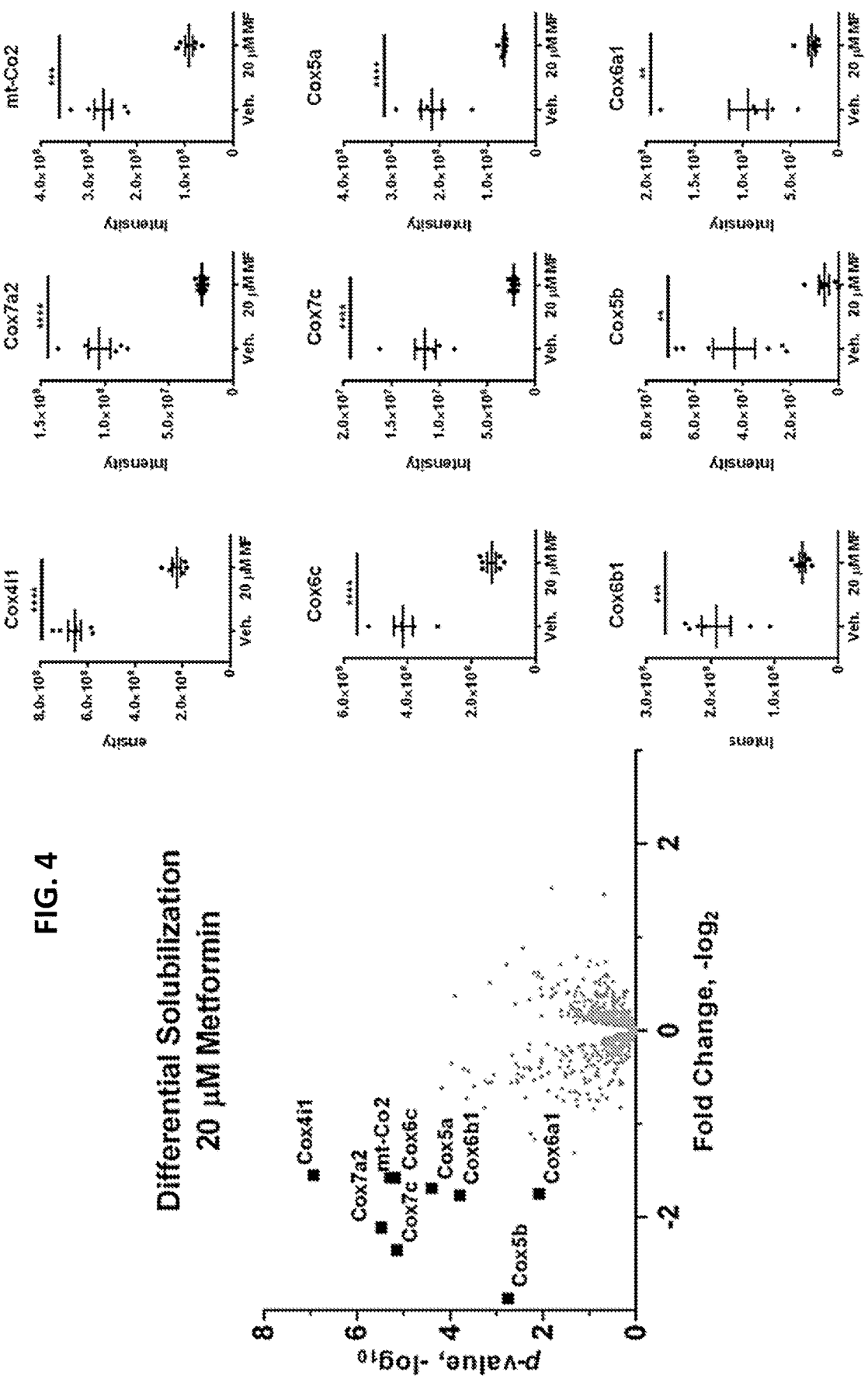
FIG. 4: Differential solubilization of membrane proteins following 20 μM metformin treatment. Volcano plot with log transform of p-value on y-axis and negative log base 2 transform of fold change on the x axis. The nine proteins identified as members of complex IV are labelled. Scattered dot plots for each protein is shown as mean and SEM and individual protein levels. Statistical analysis via Student's unpaired equal variance t-test. **, $p<0.0001$; *, $p<0.001$; **, $p<0.01$.

The nucleic acid sequences are shown using standard letter abbreviations for nucleotide base as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~15 kb), which was created on Nov. 20, 2018, and which is incorporated by reference herein.

SEQ ID NO: 1 is the amino acid sequence of Cox4i1.

SEQ ID NO: 2 is the amino acid sequence of human Cox5a.

SEQ ID NO: 3 is the amino acid sequence of human Cox6b1.

SEQ ID NO: 4 is the amino acid sequence of human Cox7a2.

SEQ ID NO: 5 is the amino acid sequence of human mt-Co2.

SEQ ID NO: 6 is the amino acid sequence of human Cox6c.

SEQ ID NO: 7 is the amino acid sequence of human Cox7c.

SEQ ID NO: 8 is the amino acid sequence of human Cox5b.

SEQ ID NO: 9 is the amino acid sequence of human Cox6a1.

SEQ ID NO: 10 is the amino acid sequence of *Mus musculus* Cox 4i1.

SEQ ID NO: 11 is the amino acid sequence of *Mus musculus* Cox5a.

SEQ ID NO: 12 is the amino acid sequence of *Mus musculus* Cox6b.

DETAILED DESCRIPTION

I. Overview

Despite being the 13$^{th}$ most prescribed drug in the U.S. and generating a billion dollars in sales annually, the molecular mechanism of metformin is not well understood. In animals and humans, metformin is absorbed through the upper small intestine, concentrated in enterocytes and hepatocytes, circulates essentially unbound, and is eliminated, unchanged, by the kidneys. At the whole-body level, metformin itself does not affect insulin sensitivity in muscle or adipose tissue but consistently reduces endogenous glucose production by inhibiting gluconeogenesis. It is accepted that the primary anti-hyperglycemic effect of metformin are a result of reduced glucose production in hepatocytes, but the exact interaction is unknown (Hundal, R. S., et al., Diabetes, 2000. 49(12): p. 2063-9). Experiments implicating the inhibition of the mitochondrial respiratory chain (complex I) (Wheaton, W. W., et al., Elife, 2014. 3: p. e02242.) activation of AMP-activated protein kinase (AMPK) pathways (Hu, M., et al., J Diabetes Res, 2016. 2016: p. 2961954), inhibition of glucagon-induced elevation of cyclic adenosine monophosphate (cAMP) with reduced activation of protein kinase A (PKA) (He, L., et al., J Biol Chem, 2016. 291(20): p. 10562-70), inhibition of mitochondrial glyceraldehyde phosphate dehydrogenase (Madiraju, A. K., et al., Nature, 2014. 510(7506): p. 542-6), and an effect on gut microbiota are proposed as potential mechanisms (Napolitano, A., et al., PLoS One, 2014. 9(7): p. e100778). The prescription uses for metformin continue to expand as additive and novel therapies for various cancers, cardiovascular diseases, neurodegenerative conditions, as well as a growing body of evidence that it has anti-aging effects (Barzilai, N., et al., Cell Metab, 2016. 23(6): p. 1060-5), which further increase the value of identifying it's mechanism of action. There are currently 327 actively-recruiting clinical trials using metformin in various capacities in 2016.

It is disclosed herein that metformin binds to Cox4i1, Cox5a, Cox6b1, Cox7a2, mt-Co2, Cox6c, Cox7c, Cox5a, Cox5b, and Cox6a1. Cytochrome c oxidase (COX) is a multi-subunit enzyme complex that couples the transfer of electrons from cytochrome c to molecular oxygen and contributes to a proton electrochemical gradient across the inner mitochondrial membrane. The complex include thirteen mitochondrial- and nuclear-encoded subunits. The mitochondrially-encoded subunits perform the electron transfer and proton pumping activities. The functions of the nuclear-encoded subunits may play a role in the regulation and assembly of the complex. The Cox4i1 gene encodes the nuclear-encoded subunit IV isoform 1 of the human mitochondrial respiratory chain enzyme. This gene is located at the 3' of the NOC4 (neighbor of COX4) gene in a head-to-head orientation. Antibodies against Cox4i1 can be used to identify the inner membrane of mitochondria in immunofluorescence studies.

Assays that measure binding to Cox4i1, Cox5a, Cox6b1, Cox7a2, mt-Co2, Cox6c, Cox7c, Cox5a, Cox5b, and Cox6a1 can be used to identify other agents that are of use to treat diabetes. In addition, agonists or antagonists of Cox4i1, Cox5a, Cox6b1, Cox7a2, mt-Co2, Cox6c, Cox7c, Cox5a, Cox5b, and Cox6a1 can be used to treat diabetes.

In further embodiments, methods are disclosed for treating a condition treatable by metformin in a patient. These methods include the steps of: (a) identifying an agent that binds to a subunit of mitochondrial electron transport complex IV, wherein the identifying comprises: (i) contacting the mitochondrial electron transport complex IV with labelled ADP and/or labelled ATP, to form an assay mixture; (ii) contacting the assay mixture with a test compound; and (iii) determining if the test compound affects binding of the labelled ADP and/or labelled ATP to the mitochondrial electron transport complex IV, as compared to binding of the labelled ADP in the absence of the test compound; wherein the test compound is identified as an agent of use in treating the condition if interferes with binding of the labelled ADP and/or labelled ATP to the mitochondrial electron transport complex IV, and (b) treating the patient with the agent.

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

α cells: Mature glucagon producing cells. In vivo, these cells are found in the pancreatic islets of Langerhans.

β cells: Mature insulin producing cells. In vivo, these cells are found in the pancreatic islets of Langerhans, δ cells: Mature somatostatin producing cells. In vivo, these cells are found in the pancreatic islets of Langerhans.

PP cells: Mature pancreatic polypeptide (PP) producing cells. In vivo, these cells are found in the pancreatic islets of Langerhans.

ε cells: Mature ghrelin producing cells. In vivo, these cells are found in the pancreatic islets of Langerhans.

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Agent: Any polypeptide, compound, small molecule, organic compound, salt, polynucleotide, or other molecule of interest. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) progression or onset of a disease.

Alteration: A statistically significant change (an increase or a decrease) in a parameter as compared to a control. In one example, an "increase" is a statistically significant elevation in a parameter, such as binding to Complex IV or a component thereof. The alternation can be measured as compared to a control. Suitable statistical analyses are well known in the art, and include, but are not limited to, Student's T test and ANOVA assays.

Animal: Living multi-cellular vertebrate organisms, a category that includes, for example, mammals and birds. The term mammal includes both human and non-human mammals. Similarly, the term "subject" includes both human and veterinary subjects.

Anti-diabetic lifestyle modifications: Changes to lifestyle, habits, and practices intended to alleviate the symptoms of diabetes or pre-diabetes. Obesity and sedentary lifestyle may both independently increase the risk of a subject developing type II diabetes, so anti-diabetic lifestyle modifications include those changes that will lead to a reduction in a subject's body mass index (BMI), increase physical activity, or both. Specific, non-limiting examples include the lifestyle interventions described in *Diabetes Care*, 22(4):623-34 at pages 626-27, herein incorporated by reference.

Complex IV: Also called cytochrome c oxidase, this is a transmembrane protein complex found in mitochondria. Complex IV is the last enzyme in the electron transport chain. It is a large complex that comprises multiple subunits including, for example, mt-Co1, mt-Co2, mt-Co3, Cox4i1, Cox4i2, Cox5a, Cox5b, Cox6b1, Cox6b2, Cox6c, Cox7a1, Cox7a2, Cox7B, Cox7b2, Cox7c, Cox8a, and Cox8c. In vivo, Complex IV receives an electron from each of four cytochrome c molecules, and transfers them to one oxygen molecule, converting molecular oxygen to two molecules of water. In the process, it binds four protons from the inner aqueous phase to make water, and in addition translocates four protons across the membrane, helping to establish a transmembrane difference of proton electrochemical potential that the ATP synthase then uses to synthesize ATP.

Control: A value used as a source for comparison with an experimentally determined value. A control can be a standard value, a ratio (such as of bound to unbound protein) from one sample, or averaged from many samples, or a baseline concentration.

Cox4i1: Also called cytochrome c oxidase subunit 4 isoform 1 is a mitochondrial enzyme and subunit of Complex IV. Cox4i1 is encoded by the COX4I1 gene. The UniProt Databank identifier for human Cox4i1 is P13073. Cox4i1 sequences are publicly available. For example, GENBANK® Accession Nos. NM_001318786.1, NM_017202.1, NM_001293559.1 disclose exemplary human, rat, and mouse Cox4i1 nucleotide sequences, respectively, and GENBANK® Accession Nos. NP_001305715.1, NP_058898.1, NP_001280488.1 disclose exemplary human, rat, and mouse Cox4i1 protein sequences, respectively. These GENBANK® entries are incorporated by reference as available on Jun. 13, 2017. One of ordinary skill in the art can identify additional Cox4i1 nucleic acid and protein sequences, including isoform and transcript variants, peptide fragments, and peptides containing phosphorylation sites.

Cox5a: Also called Cytochrome c oxidase subunit 5a is a subunit of the Complex IV. Cox5a is encoded by the COX5A gene. The UniProt Databank identifier for human Cox5a is P20674. Cox5a sequences are publicly available. For example, GENBANK® Accession Nos. NM_004255.3, NM_145783.1, NM_007747.2.1 disclose exemplary human, rat, and mouse Cox5a nucleotide sequences, respectively, and GENBANK® Accession Nos. NP_004246.2, NP_665726.1, NP_031773.2 disclose exemplary human, rat, and mouse Cox5a protein sequences, respectively. These GENBANK® entries are incorporated by reference as available on Jun. 13, 2017. One of ordinary skill in the art can identify additional Cox5a nucleic acid and protein sequences, including isoform and transcript variants, peptide fragments, and peptides containing phosphorylation sites.

Cox5b: Also called Cytochrome c oxidase subunit 5B, is a subunit of Complex IV. Cox5b is encoded by the COX5B gene. The UniProt Databank identifier for human Cox5b is P10606. Cox5b sequences are publicly available. For example, GENBANK® Accession Nos. NM_001862.2, NM_053586.1, NM_009942.2 disclose exemplary human, rat, and mouse Cox5b nucleotide sequences, respectively, and GENBANK® Accession Nos. NP_001853.2, NP_446038.1, NP_034072.2 disclose exemplary human, rat, and mouse Cox5b protein sequences, respectively. These GENBANK® entries are incorporated by reference as available on Jun. 13, 2017. One of ordinary skill in the art can identify additional Cox5b nucleic acid and protein sequences, including isoform and transcript variants, peptide fragments, and peptides containing phosphorylation sites.

Cox6a1: Also called Cytochrome c oxidase subunit 6A1, is a subunit of complex IV. Cox6a1 is encoded by the COX6A1 gene. The UniProt Databank identifier for human Cox6a1 is P12074. Cox6a1 sequences are publicly available. For example, GENBANK® Accession Nos. NM_004373.3, NM_012814.1, NM_007748.3 disclose exemplary human, rat, and mouse Cox6a1 nucleotide sequences, respectively, and GENBANK® Accession Nos. NP_004364.2, NP_036946.11, NP_031774.1 disclose exemplary human, rat, and mouse Cox6a1 protein sequences, respectively. These GENBANK® entries are incorporated by reference as available on Jun. 13, 2017. One of ordinary skill in the art can identify additional Cox6a1 nucleic acid and protein sequences, including isoform and transcript variants, peptide fragments, and peptides containing phosphorylation sites.

Cox6b1: Also called cytochrome c oxidase subunit 6B1, is a subunit of Complex IV. Cox6b1 is encoded by the COX6B1 gene. The UniProt Databank identifier for human Cox6b1 is P14854. Cox6b1 sequences are publicly available. For example, GENBANK® Accession Nos. NM_001863.4, NM_001145273.1, NM_025628.2 disclose exemplary human, rat, and mouse Cox6b1 nucleotide sequences, respectively, and GENBANK® Accession Nos. NP_001854.1, NP_001138745.1, NP_079904.1 disclose exemplary human, rat, and mouse Cox6b1protein sequences, respectively. These GENBANK® entries are incorporated by reference as available on Jun. 13, 2017. One of ordinary skill in the art can identify additional Cox6b1 nucleic acid and protein sequences, including isoform and transcript variants, peptide fragments, and peptides containing phosphorylation sites.

Cox6c: Also called cytochrome c oxidase subunit 6C, is a subunit of Complex IV. Cox6c is encoded by the COX6C gene. The UniProt Databank identifier for human Cox6c is P09669. Cox6c sequences are publicly available. For example, GENBANK® Accession Nos. NM_004374.3, M 019360.2, NM_053071.2 disclose exemplary human, rat, and mouse Cox6c nucleotide sequences, respectively, and GENBANK® Accession Nos. NP_004365.1, NP_062233.2, NP_444301.1 disclose exemplary human, rat, and mouse Cox6c protein sequences, respectively. These GENBANK® entries are incorporated by reference as available on Jun. 13, 2017. One of ordinary skill in the art can identify additional Cox6c nucleic acid and protein sequences, including isoform and transcript variants, peptide fragments, and peptides containing phosphorylation sites.

Cox7a2: Also called cytochrome c oxidase polypeptide 7A2, is a subunit of Complex IV. Cox7a2 is encoded by the COX7A2 gene. The UniProt Databank identifier for human Cox7a2 is P14406. Cox7a2 sequences are publicly available. For example, GENBANK® Accession Nos. NM_001865.3, NM_022503.2, NM_009945.3 disclose exemplary human, rat, and mouse Cox7a2 nucleotide sequences, respectively, and GENBANK® Accession Nos. NP_001856.2, NP_071948.1, NP_034075.2 disclose exemplary human, rat, and mouse Cox7a2 protein sequences, respectively. These GENBANK® entries are incorporated by reference as available on Jun. 13, 2017. One of ordinary skill in the art can identify additional Cox7a2 nucleic acid and protein sequences, including isoform and transcript variants, peptide fragments, and peptides containing phosphorylation sites.

Cox7c: Also called cytochrome c oxidase subunit 7C, is a subunit of Complex IV. Cox7c is encoded by the COX7C gene. The UniProt Databank identifier for human Cox7c is P15954. Cox7c sequences are publicly available. For example, GENBANK® Accession Nos. NM_001867.2, NM_001134705.1, NM_007749.3 disclose exemplary human, rat, and mouse Cox7c nucleotide sequences, respectively, and GENBANK® Accession Nos. NP_001858.1, NP_001128177.1, NP_031775.1 disclose exemplary human, rat, and mouse Cox7c protein sequences, respectively. These GENBANK® entries are incorporated by reference as available on Jun. 13, 2017. One of ordinary skill in the art can identify additional Cox7c nucleic acid and protein sequences, including isoform and transcript variants, peptide fragments, and peptides containing phosphorylation sites.

Determining or Measuring: Identifying the presence of a target molecule or binding to a target molecule in a sample. There terms refer to measuring a quantity or quantitating the target molecule, or binding to the target molecule, in the sample, either absolutely or relatively. The sample can be any biological sample of interest, such as, but not limited to, a plasma sample, serum sample, or tissue extract. Generally, detecting, measuring or determining a biological molecule requires performing an assay, such as mass spectrometry, and not simple observation.

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 1 diabetes mellitus is characterized by loss of the insulin-producing βcells, leading to insulin deficiency. This type can be further classified as immune-mediated or idiopathic. Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:
  a. Fasting plasma glucose level ≥7.0 mmol/l (126 mg/dl);
  b. Plasma glucose ≥11.1 mmol/l (200 mg/dL) two hours after a 75 g oral glucose load as in a glucose tolerance test;
  c. Symptoms of hyperglycemia and casual plasma glucose ≥11.1 mmol/l (200 mg/dl);
  d. Glycated hemoglobin (HbA1C)≥6.5%

Differential Mass Spectrometry (dMS): A mass spectrometry method useful for proteomics as it can differentiate peptides based on fold change. The method can differentiate the presence versus absence and a 2-fold change and lower in peptide concentration near the limit of detection of the instrument used. The method is more sensitive and gives fewer false positives than subtractive methods that ignore signal variability. The method can, for example, identify proteins that are drug bound versus unbound. The method is able to quantify thousands of proteins simultaneously from complex mixtures and has no protein size limits or minimum requirements. It can also work on protein complexes, whether covalently or noncovalently bound.

Effective amount or Therapeutically effective amount: The amount of agent that is an amount sufficient to prevent, treat (including prophylaxis), reduce and/or ameliorate the symptoms and/or underlying causes of any of a disorder or disease. In one embodiment, an "effective amount" is sufficient to reduce or eliminate a symptom of a disease, such as diabetes. In another embodiment, an effective amount is an amount sufficient to overcome the disease itself.

Endocrine: Tissue which secretes regulatory hormones directly into the bloodstream without the need for an associated duct system.

Exocrine: Secretory tissue which distributes its products, such as enzymes, via an associated duct network. The exocrine pancreas is the part of the pancreas that secretes enzymes required for digestion. The exocrine cells of the pancreas include the centroacinar cells and basophilic cells, which produce secretin and cholecystokinin.

Islets of Langerhans: Small discrete clusters of pancreatic endocrine tissue. In vivo, in an adult mammal, the islets of Langerhans are found in the pancreas as discrete clusters (islands) of pancreatic endocrine tissue surrounded by the pancreatic exocrine (or acinar) tissue. In vivo, the islets of Langerhans consist of the α cells, β cells, δ cells, PP cells, and c cells. Histologically, in rodents, the islets of Langerhans consist of a central core of β cells surrounded by an outer layer of α cells, δ cells, and PP cells. The structure of human islets of Langerhans is different and distinct from rodents. The islets of Langerhans are sometimes referred to herein as "islets."

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Mammal: This term includes both human and non-human mammals. Similarly, the term "subject" includes both human and veterinary subjects.

Mass Spectrometry: A process used to separate and identify molecules based on their mass. Mass spectrometry ionizes chemical compounds to generate charged molecules or molecule fragments and measures their mass-to-charge ratios. In a typical MS procedure, a sample is ionized. The ions are separated according to their mass-to-charge ratio, and the ions are dynamically detected by some mechanism capable of detecting energetic charged particles. The signal is processed into the spectra of the masses of the particles of that sample. The elements or molecules are identified by correlating known masses by the identified masses. "Time-of-flight mass spectrometry" (TOFMS) is a method of mass spectrometry in which an ion's mass-to-charge ratio is determined via a time measurement. Ions are accelerated by an electric field of known strength. This acceleration results in an ion having the same kinetic energy as any other ion that has the same charge. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion. "Liquid chromatography-mass spectrometry" or "LC-MS" is a chemistry technique that combines the physical separation capabilities of liquid chromatography (or HPLC) with the mass analysis capabilities of mass spectrometry. Liquid chromatography mass spectrometry (LC-MS) separates compounds chromatographically before they are introduced to the ion source and mass spectrometer. It differs from gas chromatography (GC-MS) in that the mobile phase is liquid, usually a mixture of water and organic solvents, instead of gas and the ions fragments. Most commonly, an electrospray ionization source is used in LC-MS. [PLEASE MODIFY THIS DEFINITION AS APPROPRIATE.]

Mean and Standard Deviation: The arithmetic mean is the "standard" average, often simply called the "mean".

$$\bar{x} = \frac{1}{n} \cdot \sum_{i=1}^{n} x_i$$

The mean is the arithmetic average of a set of values.

The standard deviation (represented by the symbol sigma, $\sigma$) shows how much variation or "dispersion" exists from the mean. The standard deviation of a random variable, statistical population, data set, or probability distribution is the square root of its variance. The standard deviation is commonly used to measure confidence in statistical conclusions. Generally, twice the standard deviation is about the radius of a 95 percent confidence interval. Effects that fall far outside the range of standard deviation are generally considered statistically significant. One of skill in the art can readily calculate the mean and the standard deviation from a population of values.

mt-Co2: Also called cytochrome c oxidase subunit 2, COXII, COX2, COII, and cytochrome c oxidase polypeptide II, is a subunit of Complex IV. mt-Co2 is encoded by the MT-CO2 gene. The UniProt Databank identifier for human mt-Co2 is P00403. mt-Co2 sequences are publicly available. For example, GENBANK® Accession Nos. FJ656215.1, NC_012374.1, NC_005089.1 disclose exemplary human, rat, and mouse mt-Co2 nucleotide sequences, respectively, and GENBANK® Accession Nos. ACM51349.1, YP_002791019.1, NP_904331.1 disclose exemplary human, rat, and mouse mt-Co2 protein sequences, respectively. These GENBANK® entries are incorporated by reference as available on Jun. 13, 2017. One of ordinary skill in the art can identify additional mt-Co2 nucleic acid and protein sequences, including isoform and transcript variants, peptide fragments, and peptides containing phosphorylation sites.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Octyl β-d-glucopyranoside: Also known as ocytl glucoside and OGP is a nonionic surfactant and common detergent for the solubilization of membrane proteins. OGP is a glycoside derived from glucoase and octanol. OGP has the structure shown below:

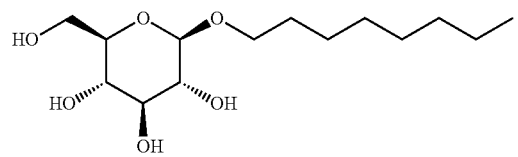 [SMILES: CCCCCCCCO[C@@H]1O[C@H](CO)[C@@H](O)[C@H](O)[C@H]1O]

Pancreatic endocrine cell: An endocrine cell of pancreatic origin that produces one or more pancreatic hormone, such as insulin, glucagon, somatostatin, or pancreatic polypeptide. Subsets of pancreatic endocrine cells include the α (glucagon producing), β (insulin producing) δ (somatostatin producing) or PP (pancreatic polypeptide producing) cells. Additional subsets produce more than one pancreatic hormone, such as, but not limited to, a cell that produces both insulin and glucagon, or a cell that produces insulin, glucagon, and somatostatin, or a cell that produces insulin and somatostatin.

Pre-diabetes: A state in which some, but not all, of the criteria for diabetes are met. For example, a subject can have impaired fasting glycaemia or impaired fasting glucose (IFG). Subjects with fasting glucose levels from 110 to 125 mg/dl (6.1 to 6.9 mmol/1) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

Predisposition for diabetes: A subject that is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m$^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" Diabetes Care 25(1): S5-S24 (2002).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or a composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Sequence identity of amino acid sequences: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a protein are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a β cell specific binding agent is an agent that binds substantially to a β cell, and a pancreatic endocrine cell specific binding agent is an gent that binds substantially only to pancreatic endocrine cells or a subset thereof (and not to pancreatic exocrine cells). Similarly, a pancreatic exocrine cell specific binding agent is an agent that binds substantially to exocrine cells. In one embodiment, the specific binding agent is a monoclonal or polyclonal antibody that specifically binds a type of pancreatic cell.

The term "specifically binds" refers, with respect to a cell, such as a pancreatic endocrine cell, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Any mammal, such as humans, non-human primates, pigs, sheep, cows, rodents and the like which is to be the recipient of the particular treatment. In two non-limiting examples, a subject is a human subject or a murine subject.

Therapeutic agent: Used in a generic sense, it includes treating agents, prophylactic agents, and replacement agents. The agent can be any molecule, such as a chemical compound, antibody, small molecule, protein, oligosaccharide, or glycoprotein used for the treatment of a disorder. In some embodiments, therapeutic agent can be an antibody that specifically binds pancreatic endocrine cells or a subset thereof.

Under conditions sufficient for: A phrase that is used to describe any environment that permits the desired activity.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Screening Methods

Mitochondrial electron transport complex IV (cytochrome c oxidase) subunits, such as Cox4i1, Cox5a, Cox6b1, Cox7a2, mt-Co2, Cox6c, Cox7c, Cox5a, Cox5b, and Cox6a1 are a binding target of metformin. Complex IV is the terminal enzyme in the electron transport chain and responsible for generating the transmembrane electrochemical gradient required by ATP synthase to generate ATP, and is comprised of 14 subunits that span the phospholipid bilayer of the mitochondria. Three of the subunits are synthesized in the mitochondria and responsible for the electron gradient and proton pumping functions of the complex. The remaining 11, including Cox4i1, are nuclear encoded and appear to be involved in the regulation of activity and assembly of the complex. Cox4i1 itself is located on the lumen-facing side of the inner membrane and studies have shown that it can be allosterically inhibited by both high intra- and extramitochondrial ATP/ADP ratios (Arnold, S. and B. Kadenbach, Eur J Biochem, 1997. 249(1): p. 350-4; Frank, V. and B. Kadenbach, FEBS Lett, 1996. 382(1-2): p. 121-4; Beauvoit, B. and M. Rigoulet, IUBMB Life, 2001. 52(3-5): p. 143-52). Metformin, a very hydrophilic molecule, mimics the electronegative charge distribution and sterics of ATP in the cell, recapitulating the inhibition by excess ATP when present in biological levels.

Screening methods of use can take advantage of ligand/protein stabilization by disordering the system—through heat or chemical denaturation. A ligand bound protein is a stable protein, so it can withstand more heat or chemical denaturation prior to agglutination/precipitation. Detergents are needed to study insoluble membrane proteins. Detergents can actually improve the ability of proteins to withstand heat/denaturants and their resultant interference with complex function. Thus, the disclosed methods can include a step of contacting a membrane with a detergent, such as, but not limited to, Octyl β-d-glucopyranoside (also known as ocytl glucoside, OGP) and N-Dodecyl-β-D-maltoside (also known as dodecyl maltoside, DDM). The detergents used must maintain native state of membrane proteins and complexes while retaining binding ability and have mass spec compatibility, excluding the majority of detergents from applicability. Screening methods of use can include determining if the test compound binds a subunit of the mitochondrial electron transport complex IV, and/or alters the function of the mitochondrial electron transport complex IV.

Some methods of use rely on the known changes to conformational stability that occur in ligand binding for membrane proteins when attempting to detergent solubilize. A different proportion of protein will solubilize in the same amount of detergent if it is/is not bound to a ligand. This difference can be utilized to identify bound agents. After solubilization in the presence of ligand, non-solubilized proteins are removed and analyzed, measuring differences using differential mass spectrometry (dMS). The method also allows for a titration as in more traditional methods, but instead of heat or chemical denaturant titration, detergent concentration can be titrated. A different amount of detergent may be required for solubilization of a protein compared to the same protein in its ligand bound or protein complex conformation.

The assay can be a functional assay. A functional assay can be performed in (a) whole mitochondria or reconstituted liposomes "proteasomes" (see Arnold and Kadenbach, Eur J Biochem, 1997. 249(1): p. 350-4; Frank and Kadenbach, FEBS Lett, 1996. 382(1-2): p. 121-4; Yoshikawa et al., Proc Natl Acad Sci USA, 1988. 85(5): p. 1354-8; Anthony et al., Proc Natl Acad Sci USA, 1993. 90(5): p. 1652-6, all incorporated by reference); of complex IV, either normal or inverted (Huther and Kadenbach, Biochem Biophys Res Commun, 1988. 153(2): p. 525-34; Hunther and Kadenbach, Biochem Biophys Res Commun, 1987. 147(3): p. 1268-75, all incorporated by reference). These assays allow for control of intramembrane space ATP/ADP ratios and hypo-hypertonicity, and liposomes can be inverted for control of matrix space. These assays provide better specificity in reconstituted liposomes of only complex IV. The assays can measure H+/e− stoichiometry for functional assay. For example, the assay can use safranin O, mitosox, or FluoVolt to monitor fluorescence changes (see, Drahota et al., Physiol Res, 2014. 63(1): p. 1-11; Ashakura et al., J Pharmacol Toxicol Methods, 2015. 75: p. 17-26, all incorporated herein by reference). These assays are readily industrialized and automated.

Binding assays are also of use. A binding assay can be a mass spectrometry assay based, such as the method disclosed below. The samples can be run in this assay with and without ligand, and then intensity differences in ligand vs. vehicle can be interrogated using a triple quad using known transitions (fragment ions from specific precursor peptides) for Complex IV. Only binders cause a significant difference in intensity due to solubility changes with ligand. This is a high throughput targeted version of the discovery methodology. These assays are specific to smallest unit in detergent (can be single proteins, can be complexes).

Displacement based binding assays can also be used. Without being bound by theory, ATP and ADP can bind COX4i1 and COX6a to alter expression (matrix side COX4i1 ATP binding is inhibitory in hypertonic solution, COX6a intramembrane space ATP binding excitatory in hypotonic solution) (see, for example, Beauvoit et al., IUBMB Life, 2001. 52(3-5): p. 143-52, incorporated by reference herein). Reconstituted liposomes "proteasomes" (see Arnold and Kadenback, supra; Frank and Kadenbach, supra; Yoshikawa et al., supra; Anthony et al., supra, all incorporated by reference herein) of complex IV, either normal or inverted (see Huther and Kadenbach, 1988, supra; Huther and Kadenbach, 1987, supra, incorporated by reference herein). In these assays, normal allows for control of intramembrane space ATP/ADP ratios and hypo-hypertonicity, inverted for control of matrix space.

A labeled molecule, such as a fluorescent or radiolabeled ATP and ADP can be used, specifically in a displacement assay to identify small molecule drugs. A displacement assay measures displacement (differential fluorescence or radiation) as a marker of drug binding. In some embodiments, a displacement assay can be specific to subunit, such as for ATP or ADP binding sites on COX4i1 and COX6a.

U.S. Pat. No. 6,906,320 "Mass Spectrometry Data Analysis Techniques," incorporated herein by reference discloses methods for identification using mass spectrometry. These methods were modified for the work herein disclosed. As disclosed in U.S. Patent Application No. 2015/0133336, a feature of cellular thermal shift assay (CETSA) methodology is the use of heat to alter the stability of the protein. Others have employed other methods, such as chemical denaturation, to also cause this change. The findings disclosed herein demonstrate that the use of detergents, not heat, could be useful and important to study drug/protein binding interactions. An exemplary method that utilizes mass spectrometry is disclosed below. This assay can be of use for identifying agents of interest.

In some embodiments, a screening assay measures binding to liver membrane proteins. In some embodiments, liver tissue from a mammal, including human and/or veterinary subjects (for example, mouse or human liver tissue) is homogenized and centrifuged to pellet cell membranes retaining membrane bound proteins. Membrane bound proteins can be incubated with an agent, such as metformin or any test agent of interest, and the unbound agent washed away after an incubation period of about 10-20, about 12-18, or about 15 minutes. The agent can be added at physiologically relevant concentrations, e.g. about 5 µM, about 10 µM, about 15 µM, about 20 µM, about 30 µM, about 40 µM, about 50 µM, about 60 µM, about 70 µM, about 80 µM, about 90 µM, about 100 µM, or more. Physiologically relevant dosage ranges can differ for various drugs or agents. Following incubation with the agent, bound membrane proteins can be solubilized in detergent, e.g. octyl-glucoside or dodecyl maltoside. In some embodiments, bound membrane proteins can be digested, e.g. by trypsin digest, into peptides of suitable length for mass spectrometry.

In some embodiments, membrane proteins incubated with drug can be compared to control membrane proteins that have not been incubated with drug and both control and drug-incubated samples subjected to mass spectrometry. Those liver membrane proteins bound to drug can be identified by differential mass spectrometry (dMS). dMS finds significant differences in intensity of high-abundance and low-abundance ions. This significant difference can be used to identify those proteins which are bound to a drug. The proteins can be further identified by targeted MS/MS analysis.

IV. Compounds of Use

It is disclosed herein that any agent or compound that binds a subunit of the mitochondrial electron transport complex IV, and/or alters the function of the mitochondrial electron transport complex IV (wherein the agent is not metformin), such as biguanides, can be used to treat conditions that are treatable by metformin. There conditions include, but are not limited to, cancers, cardiovascular diseases, neurodegenerative conditions, and type II diabetes.

In some embodiments, the agent of use in the methods disclosed herein specifically binds a subunit of the mitochondrial electron transport complex IV, such as Cox4i1, Cox5a, Cox6b1, Cox7a2, mt-Co2, Cox6c, Cox7c, Cox5b, and/or Cox6a1.

An exemplary amino acid sequence of human Cox4i1 is shown below (see also UNIPROTKB No. P13073, incorporated herein by reference, see also FIG. 2).

```
                                            (SEQ ID NO: 1)
MLATRVFSLV GKRAISTSVC VRAHESVVKS EDFSLPAYMD

RRDHPLPEVA HVKHLSASQK ALKEKEKASW SSLSMDEKVE

LYRIKFKESF AEMNRGSNEW KTVVGGAMFF IGFTALVIMW

QKHYVYGPLP QSFDKEWVAK QTKRMLDMKV NPIQGLASKW

DYEKNEWKK.
```

In other embodiments, the agent of use in the methods disclosed herein specifically binds Cox5a or Cox6B. The amino acid sequence of *Mus musculus* Cox5a and Cox 6B are also provided in FIG. 2.

The amino acid sequence of human Cox5a is shown below.

```
                                            (SEQ ID NO: 2)
MLGAALRRCA VAATTRADPR GLLHSARTPG PAVAIQSVRC

YSHGSQETDE EFDARWVTYF NKPDIDAWEL RKGINTLVTY

DMVPEPKIID AALRACRRLN DFASTVRILE VVKDKAGPHK

EIYPYVIQEL RPTLNELGIS TPEELGLDKV.
```

The amino acid sequence of human Cox6b1 is shown below.

```
                                            (SEQ ID NO: 3)
MAVVGVSSVS RLLGRSRPQL GRPMSSGAHG EEGSARMWKT

LTFFVALPGV AVSMLNVYLK SHHGEHERPE FIAYPHLRIR

TKPFPWGDGN HTLFHNPHVN PLPTGYEDE.
```

The amino acid sequence of human Cox7a2 is shown below.

```
                                            (SEQ ID NO: 4)
MHTQDSEVVP VPAWPFSLVV FSCGGCWSVT AKMLRNLLAL

RQIGQRTIST ASRRHFKNKV PEKQKLFQED DEIPLYLKGG

VADALLYRAT MILTVGGTAY AIYELAVASF PKKQE.
```

The amino acid sequence of human mt-Co2 is shown below.

```
                                            (SEQ ID NO: 5)
MAHAAQVGLQ DATSPIMEEL ITFHDHALMI IFLICFLVLY

ALFLTLTTKL TNTNISDAQE METVWTILPA IILVLIALPS

LRILYMTDEV NDPSLTIKSI GHQWYWTYEY TDYGGLIFNS

YMLPPLFLEP GDLRLLDVDN RVVLPIEAPI RMMITSQDVL

HSWAVPTLGL KTDAIPGRLN QTTFTATRPG VYYGQCSEIC

GANHSFMPIV LELIPLKIFE MGPVFTL.
```

The amino acid sequence of human Cox6c is shown below.

```
                                            (SEQ ID NO: 6)
MAPEVLPKPR MRGLLARRLR NHMAVAFVLS LGVAALYKFR

VADQRKKAYA DFYRNYDVMK DFEEMRKAGI FQSVK.
```

The amino acid sequence of human Cox7c is shown below.

```
                                            (SEQ ID NO: 7)
MLGQSIRRFT TSVVRRSHYE EGPGKNLPFS VENKWSLLAK

MCLYFGSAFA TPFLVVRHQL LKT.
```

The amino acid sequence of human Cox5b is shown below.

```
                                            (SEQ ID NO: 8)
MASRLLRGAG TLAAQALRAR GPSGAAAMRS MASGGGVPTD

EEQATGLERE IMLAAKKGLD PYNVLAPKGA SGTREDPNLV

PSISNKRIVG CICEEDNTSV VWFWLHKGEA QRCPRCGAHY

KLVPQQLAH.
```

The amino acid sequence of human Cox6a1 is shown below.

```
                                            (SEQ ID NO: 9)
MAVVGVSSVS RLLGRSRPQL GRPMSSGAHG EEGSARMWKT

LTFFVALPGV AVSMLNVYLK SHHGEHERPE FIAYPHLRIR

TKPFPWGDGN HTLFHNPHVN PLPTGYEDE.
```

An agonist of mitochondrial electron transport complex IV, such as an agonist of Cox4i1, Cox5a, Cox6b1, Cox7a2, mt-Co2, Cox6c, Cox7c, Cox5b, and/or Cox6a1 is any agent having the ability to increase the expression or the activity of mitochondrial electron transport complex IV (e.g. Cox4i1, Cox5a, Cox6b1, Cox7a2, mt-Co2, Cox6c, Cox7c, Cox5b, or Cox6a1) in a cell. The activity of the mitochondrial electron transport complex IV, or the activity and/or expression of Cox4i1, Cox5a, Cox6b1, Cox7a2, mt-Co2, Cox6c, Cox7c, Cox5b, or Cox6a1 is reduced by at least about 10%, 20%, 30%, 40%, 50%, 60%, 70%, 80%, 90%, 100%, 200%, 300%, or more, compared to such expression or activity in a control. Exemplary increases in activity are at least about 50%, at least about 60%, at least about 70%, at least about 80%, at least about 90%, at least about 95%, or at least about 100%. In one example, the control is a cell that has not been treated with the agonist. In another example, the control is a standard value, or a cell contacted with an agent, such as a carrier, known not to affect activity. Expression or activity can be determined by any standard method in the art, including those described herein.

An antagonist of mitochondrial electron transport complex IV, such as an antagonist of Cox4i1, Cox5a, Cox6b1, Cox7a2, mt-Co2, Cox6c, Cox7c, Cox5b, or Cox6a1 is any agent having the ability to reduce the expression or the activity of mitochondrial electron transport proteins Cox4i1, Cox5a, Cox6b1, Cox7a2, mt-Co2, Cox6c, Cox7c, Cox5b, or Cox6a1 in a cell. The activity of the mitochondrial electron transport complex IV, or the activity and/or expression of Cox4i1, Cox5a, Cox6b1, Cox7a2, mt-Co2, Cox6c, Cox7c, Cox5b, or Cox6a1 is reduced by at least about 10%, 20%, 30%, 40%, 50%, 60%, 70%, 80%, 90%, or 100% compared to such expression or activity in a control. Exemplary reductions in activity are at least about 50%, at least about 60%, at least about 70%, at least about 80%, at least about 90%, at least about 95%, or a complete absence of detectable activity/expression. In one example, the control is a cell that has not been treated with the antagonist. In another example, the control is a standard value, or a cell contacted with an agent, such as a carrier, known not to affect activity. Expression or activity can be determined by any standard method in the art, including those described herein.

A. Small Molecule Agonists and Antagonists

Agonists and antagonists of mitochondrial electron transport complex IV, such as an agonist or antagonist of Cox4i1, Cox5a, Cox6b1, Cox7a2, mt-Co2, Cox6c, Cox7c, Cox5b, or Cox6a1 include molecules that are identified from large libraries of both natural product or synthetic (or semi-synthetic) extracts or chemical libraries according to methods known in the art. The screening methods that detect decreases increases in activity and/or binding (see above), are useful for identifying compounds from a variety of sources for activity. The initial screens may be performed using a diverse library of compounds, a variety of other compounds and compound libraries. These small molecules can be identified from combinatorial libraries, natural product libraries, or other small molecule libraries. In addition, an antagonist or an agonist can be identified as compounds from commercial sources, as well as commercially available analogs of identified inhibitors.

The precise source of test extracts or compounds is not critical to the identification. Accordingly, agonists or antagonists can be identified from virtually any number of chemical extracts or compounds. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Compounds can be identified from synthetic compound libraries that are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Compounds can be identified from a rare chemical library, such as the library that is available from Aldrich (Milwaukee, Wis.). Cox4i1, Cox5a, Cox6b1, Cox7a2, mt-Co2, Cox6c, Cox7c, Cox5b, or Cox6a1 antagonists and agonists can be identified in libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, such as less than about 750 or less than about 350 daltons can be utilized in the methods disclosed herein. Exemplary classes include heterocycles, peptides, saccharides, steroids, and the like. The compounds may be modified to enhance efficacy, stability, pharmaceutical compatibility, and the like. In several embodiments, compounds of use has a Kd for a submit of the mitochondrial electron transport complex IV (e.g. Cox4i1, Cox5a, Cox6b1, Cox7a2, mt-Co2, Cox6c, Cox7c, Cox5b, or Cox6a1) of less than 1 nM, less than 10 nm, less than 1 µM, less than 10 µM, or less than 1 mM.

B. Inhibitory Nucleic Acids

In some non-limiting embodiments, inhibitory nucleic acids that decrease the expression and/or activity of the mitochondrial electron transport complex IV, such as Cox4i1, Cox5a, Cox6b1, Cox7a2, mt-Co2, Cox6c, Cox7c, Cox5b, or Cox6a1 can be used in the methods disclosed herein. One embodiment is a small inhibitory RNA (siRNA) for interference or inhibition of expression of a target gene. Nucleic acid sequences encoding Cox4i1, Cox5a, Cox6b1, Cox7a2, mt-Co2, Cox6c, Cox7c, Cox5b, and Cox6a1 are disclosed in GENBANK®, with exemplary amino acid sequences and GENBANK® Accession numbers of each listed herein.

Generally, siRNAs are generated by the cleavage of relatively long double-stranded RNA molecules by Dicer or DCL enzymes (Zamore, Science, 296:1265-1269, 2002; Bernstein et al., Nature, 409:363-366, 2001). In animals and plants, siRNAs are assembled into RISC and guide the sequence specific ribonucleolytic activity of RISC, thereby resulting in the cleavage of mRNAs or other RNA target molecules in the cytoplasm. In the nucleus, siRNAs also guide heterochromatin-associated histone and DNA methylation, resulting in transcriptional silencing of individual genes or large chromatin domains. Complex IV subunit siRNAs are commercially available, such as from Santa Cruz Biotechnology, Inc.

The present disclosure provides RNA suitable for interference or inhibition of expression of a target gene, which RNA includes double stranded RNA of about 15 to about 40 nucleotides containing a 0 to 5-nucleotide 3' and/or 5' overhang on each strand. The sequence of the RNA is substantially identical to a portion of an mRNA or transcript of a target gene, such as Cox4i1, Cox5a, Cox6b1, Cox7a2, mt-Co2, Cox6c, Cox7c, Cox5b, or Cox6a1) for which interference or inhibition of expression is desired. For purposes of this disclosure, a sequence of the RNA "substantially identical" to a specific portion of the mRNA or transcript of the target gene for which interference or inhibition of expression is desired differs by no more than about 30 percent, and in some embodiments no more than about 10 percent, from the specific portion of the mRNA or transcript of the target gene. In particular embodiments, the sequence of the RNA is exactly identical to a specific portion of the mRNA or transcript of the target gene.

Thus, siRNAs disclosed herein include double-stranded RNA of about 15 to about 40 nucleotides in length and a 3' or 5' overhang having a length of 0 to 5-nucleotides on each strand, wherein the sequence of the double stranded RNA is substantially identical to (see above) a portion of a mRNA or transcript of a nucleic acid encoding Cox4i1, Cox5a, Cox6b1, Cox7a2, mt-Co2, Cox6c, Cox7c, Cox5b, or Cox6a1. In particular examples, the double stranded RNA contains about 19 to about 25 nucleotides, for instance 20, 21, or 22 nucleotides substantially identical to a nucleic acid encoding Cox4i1, Cox5a, Cox6b1, Cox7a2, mt-Co2, Cox6c, Cox7c, Cox5b, or Cox6a1. In additional examples, the double stranded RNA contains about 19 to about 25 nucleotides 100% identical to a nucleic acid encoding Cox4i1, Cox5a, Cox6b1, Cox7a2, mt-Co2, Cox6c, Cox7c, Cox5b, or Cox6a1. It should be noted that in this context "about" refers to integer amounts only. In one example, "about" 20 nucleotides refers to a nucleotide of 19 to 21 nucleotides in length.

Regarding the overhang on the double-stranded RNA, the length of the overhang is independent between the two strands, in that the length of one overhang is not dependent on the length of the overhang on other strand. In specific examples, the length of the 3' or 5' overhang is 0-nucleotide on at least one strand, and in some cases it is 0-nucleotide on both strands (thus, a blunt dsRNA). In other examples, the length of the 3' or 5' overhang is 1-nucleotide to 5-nucleotides on at least one strand. More particularly, in some examples the length of the 3' or 5' overhang is 2-nucleotides on at least one strand, or 2-nucleotides on both strands. In particular examples, the dsRNA molecule has 3' overhangs of 2-nucleotides on both strands.

Thus, in one particular provided RNA embodiment, the double-stranded RNA contains 20, 21, or 22 nucleotides, and the length of the 3' overhang is 2-nucleotides on both strands. In embodiments of the RNAs provided herein, the double-stranded RNA contains about 40-60% adenine+uracil (AU) and about 60-40% guanine+cytosine (GC). More particularly, in specific examples the double-stranded RNA contains about 50% AU and about 50% GC.

Also described herein are RNAs that further include at least one modified ribonucleotide, for instance in the sense strand of the double-stranded RNA. In particular examples, the modified ribonucleotide is in the 3' overhang of at least one strand, or more particularly in the 3' overhang of the sense strand. It is particularly contemplated that examples of modified ribonucleotides include ribonucleotides that include a detectable label (for instance, a fluorophore, such as rhodamine or FITC), a thiophosphate nucleotide analog, a deoxynucleotide (considered modified because the base molecule is ribonucleic acid), a 2'-fluorouracil, a 2'-aminouracil, a 2'-aminocytidine, a 4-thiouracil, a 5-bromouracil, a 5-iodouracil, a 5-(3-aminoallyl)-uracil, an inosine, or a 2'O-Me-nucleotide analog.

Antisense and ribozyme molecules for Cox4i1, Cox5a, Cox6b1, Cox7a2, mt-Co2, Cox6c, Cox7c, Cox5b, or Cox6a1 are also of use in the methods disclosed herein. Antisense nucleic acids are DNA or RNA molecules that are complementary to at least a portion of a specific mRNA molecule (Weintraub, *Scientific American* 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target cell producing Cox4i1, Cox5a, Cox6b1, Cox7a2, mt-Co2, Cox6c, Cox7c, Cox5b, or Cox6a1. The use of antisense methods to inhibit the in vitro translation of genes is well known in the art (see, for example, Marcus-Sakura, *Anal. Biochem.* 172:289, 1988).

An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid molecule can be chemically synthesized using naturally occurring nucleotides or variously modified nucleotides designed to increase the biological stability of the molecules or to increase the physical stability of the duplex formed between the antisense and sense nucleic acids, such as phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridin-e, 5-carboxymethylaminomethyluracil, dihydrouracil, beta-D-galactosylqueosine, inosine, amongst others.

Use of an oligonucleotide to stall transcription is known as the triplex strategy since the bloomer winds around double-helical DNA, forming a three-strand helix. Therefore, these triplex compounds can be designed to recognize a unique site on a chosen gene (Maher, et al., *Antisense Res. and Dev.* 1(3):227, 1991; Helene, C., *Anticancer Drug Design* 6(6):569), 1991. This type of inhibitory oligonucleotide is also of use in the methods disclosed herein.

Ribozymes, which are RNA molecules possessing the ability to specifically cleave other single-stranded RNA in a manner analogous to DNA restriction endonucleases, are also of use. Through the modification of nucleotide sequences which encode these RNAs, it is possible to engineer molecules that recognize specific nucleotide sequences in an RNA molecule and cleave it (Cech, *J. Amer. Med. Assn.* 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

Various delivery systems are known and can be used to administer the siRNAs and other inhibitory nucleic acid molecules as therapeutics. Such systems include, for example, encapsulation in liposomes, microparticles, microcapsules, nanoparticles, recombinant cells capable of expressing the therapeutic molecule(s) (see, e.g., Wu et al., *J. Biol. Chem.* 262, 4429, 1987), construction of a therapeutic nucleic acid as part of a retroviral or other vector, and the like.

C. Cox4i1, Cox5a, Cox6b1, Cox7a2, mt-Co2, Cox6c, Cox7c, Cox5b, or Cox6a1 Peptide Variants as Agonists or Antagonists In one embodiment, variants of a Cox4i1, Cox5a, Cox6b1, Cox7a2, mt-Co2, Cox6c, Cox7c, Cox5b, or Cox6a1 protein which function as an agonist or an antagonist can be identified by screening combinatorial libraries of mutants, such as point mutants or truncation mutants, of a Cox4i1, Cox5a, Cox6b1, Cox7a2, mt-Co2, Cox6c, Cox7c, Cox5b, or Cox6a1 protein to identify proteins with agonist or antagonist activity.

Thus, a library of Cox4i1, Cox5a, Cox6b1, Cox7a2, mt-Co2, Cox6c, Cox7c, Cox5b, or Cox6a1 variants can be generated by combinatorial mutagenesis at the nucleic acid level and is encoded by a variegated gene library. A library of Cox4i1, Cox5a, Cox6b1, Cox7a2, mt-Co2, Cox6c, Cox7c, Cox5b, or Cox6a1 variants can be produced by, for example, by enzymatically ligating a mixture of synthetic oligonucleotides into gene sequences such that a degenerate set of potential Cox4i1, Cox5a, Cox6b1, Cox7a2, mt-Co2, Cox6c, Cox7c, Cox5b, or Cox6a1 sequences is expressible as individual polypeptides, or alternatively, as a set of larger fusion proteins (such as for phage display) containing the set of Cox4i1, Cox5a, Cox6b1, Cox7a2, mt-Co2, Cox6c, Cox7c, Cox5b, or Cox6a1 sequences.

There are a variety of methods which can be used to produce libraries of potential Cox4i1, Cox5a, Cox6b1, Cox7a2, mt-Co2, Cox6c, Cox7c, Cox5b, or Cox6a1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Cox4i1 antagonist sequences. Methods for synthesizing degenerate oligonucleotides are known in the art (see, for example, Narang, et al., Tetrahedron 39:3, 1983; Itakura et al. Annu. Rev. Biochem. 53:323, 1984; Itakura et al. Science 198:1056, 1984).

In addition, libraries of fragments of a Cox4i1, Cox5a, Cox6b1, Cox7a2, mt-Co2, Cox6c, Cox7c, Cox5b, or Cox6a1 protein coding sequence can be used to generate a population of Cox4i1, Cox5a, Cox6b1, Cox7a2, mt-Co2, Cox6c, Cox7c, Cox5b, or Cox6a1 fragments for screening and subsequent selection of variants of a Cox4i1, Cox5a, Cox6b1, Cox7a2, mt-Co2, Cox6c, Cox7c, Cox5b, or Cox6a1 antagonist. In one embodiment, a library of coding sequence fragments can be generated by treating a double stranded PCR fragment of a Cox4i1, Cox5a, Cox6b1, Cox7a2, mt-Co2, Cox6c, Cox7c, Cox5b, or Cox6a1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with 51 nuclease, and ligating the resulting fragment library into an expression vector. By this method, an expression library can be derived which encodes N-terminal, C-terminal and internal fragments of various sizes of Cox4i1, Cox5a, Cox6b1, Cox7a2, mt-Co2, Cox6c, Cox7c, Cox5b, or Cox6a1.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Cox4i1, Cox5a, Cox6b1, Cox7a2, mt-Co2, Cox6c, Cox7c, Cox5b, or Cox6a1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM) can be used in combination with the screening assays to identify Cox4i1 antagonists (Arkin and Youvan, Proc. Natl. Acad. Sci. USA 89:7811 7815, 1992; Delagrave et al., Protein Eng. 6(3):327 331, 1993).

In one embodiment, cell based assays can be exploited to analyze a library of Cox4i1, Cox5a, Cox6b1, Cox7a2, mt-Co2, Cox6c, Cox7c, Cox5b, or Cox6a1 variants. For example, a library of expression vectors can be transfected into a cell line which ordinarily synthesizes and secretes Cox4i1, Cox5a, Cox6b1, Cox7a2, mt-Co2, Cox6c, Cox7c, Cox5b, or Cox6a1. The transfected cells are then cultured such that Cox4i1, Cox5a, Cox6b1, Cox7a2, mt-Co2, Cox6c, Cox7c, Cox5b, or Cox6a1 and a particular Cox4i1, Cox5a, Cox6b1, Cox7a2, mt-Co2, Cox6c, Cox7c, Cox5b, or Cox6a1 variant are secreted. The effect of expression of the mutant on Cox4i1, Cox5a, Cox6b1, Cox7a2, mt-Co2, Cox6c, Cox7c, Cox5b, or Cox6a1 activity in cell supernatants can be detected, such as by any of a functional assay. Plasmid DNA can then be recovered from the cells wherein endogenous Cox4i1 activity is inhibited, and the individual clones further characterized.

Peptidomimetics can also be used as Cox4i1, Cox5a, Cox6b1, Cox7a2, mt-Co2, Cox6c, Cox7c, Cox5b, or Cox6a1 antagonists. Peptide analogs are commonly used in the pharmaceutical industry as non-peptide drugs with properties analogous to those of the template peptide. These types of non-peptide compounds and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (for example, polypeptide that has a Cox4i1 biological activity), but has one or more peptide linkages optionally replaced by a $-CH_2NH-$, $-CH_2S-$, $-CH_2-CH_2-$, $-CH=CH-$ (cis and trans), $-COCH_2-$, $-CH(OH)CH_2-$, and $-CH_2SO-$ linkages. These peptide linkages can be replaced by methods known in the art (see, for example, Morley, Trends Pharm. Sci. pp. 463 468, 1980; Hudson et al. Int. J. Pept. Prot. Res. 14:177 185, 1979; Spatola, Life Sci. 38:1243 1249, 1986; Holladay, et al. Tetrahedron Lett. 24:4401 4404, 1983). Peptide mimetics can be procured economical, be stable, and can have increased have-life or absorption. Labeling of peptidomimetics usually involves covalent attachment of one or more labels, directly or through a spacer (such as by an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization of peptidomimetics should not substantially interfere with the desired biological or pharmacological activity of the peptidomimetic.

A dominant negative protein or a nucleic acid encoding a dominant negative protein that interferes with the biological activity of Cox4i1, Cox5a, Cox6b1, Cox7a2, mt-Co2, Cox6c, Cox7c, Cox5b, or Cox6a1 (i.e. binding of Cox4i1, Cox5a, Cox6b1, Cox7a2, mt-Co2, Cox6c, Cox7c, Cox5b, or Cox6a1 to metformin, or in the mitochondrial electron transport IV complex) can also be used in the methods disclosed herein, when antagonist activity is desirable. A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative Cox4i1, Cox5a, Cox6b1, Cox7a2, mt-Co2, Cox6c, Cox7c, Cox5b, or Cox6a1 has mutation such that it binds Cox4i1, Cox5a, Cox6b1, Cox7a2, mt-Co2, Cox6c, Cox7c, Cox5b, or Cox6a1 more tightly than native (wild-type) Cox4i1, Cox5a, Cox6b1, Cox7a2, mt-Co2, Cox6c, Cox7c, Cox5b, or Cox6a1, respectively, but does not provide cyclooxygenase activity in the complex.

The dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein systemically or to the infected area using, for example, microinjection techniques.

Polypeptide antagonists can be produced in prokaryotic or eukaryotic host cells by expression of polynucleotides encoding the amino acid sequence, frequently as part of a larger polypeptide (a fusion protein, such as with ras or an enzyme). Alternatively, such peptides can be synthesized by chemical methods. Methods for expression of heterologous proteins in recombinant hosts, chemical synthesis of polypeptides, and in vitro translation are well known in the art (see Maniatis el al. Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Kaiser et al., Science 243:187, 1989; Merrifield, Science 232:342, 1986; Kent, Annu. Rev. Biochem. 57:957, 1988).

Peptides can be produced, such as by direct chemical synthesis, and used as antagonists of a Cox4i1, Cox5a, Cox6b1, Cox7a2, mt-Co2, Cox6c, Cox7c, Cox5b, or Cox6a1 interaction with another member of the complex. Peptides can be produced as modified peptides, with non-peptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (for example, acetylation) or alkylation (for example, methylation) and carboxy-terminal-modifications such as amidation, as well as other terminal modifications, including cyclization, can be incorporated into various embodiments. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others.

V. Treatment of Diabetes

In some examples, the method includes selecting a subject with diabetes, such as type II diabetes, or a subject at risk for diabetes, such as a subject with pre-diabetes. These subjects can be selected for treatment. Generally, the subject is not treated with metformin. However, the subject can also be treated with metformin. The methods include the administration of a therapeutically effective amount of a compound disclosed herein, or a therapeutically effective amount of a compound identified by the methods disclosed herein.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An oral glucose tolerance test (OGTT) two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care* 33:S11-61, 2010, incorporated herein by reference).

In some examples, treating diabetes includes one or more of increasing glucose tolerance, decreasing insulin resistance (for example, decreasing plasma glucose levels, decreasing plasma insulin levels, or a combination thereof), decreasing serum triglycerides, decreasing free fatty acid levels, and decreasing HbA1c levels in the subject. In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of a compound identified using the methods disclosed herein treats diabetes, such as type II diabetes, or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, 15%, 20%, 25%, 30%, 35%, or more) as compared with a control. In particular examples, a decrease in blood glucose level is determined relative to the starting blood glucose level of the subject (for example, prior to treatment). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In other embodiments, the disclosed methods include comparing one or more indicator of diabetes (such as glucose tolerance, triglyceride levels, free fatty acid levels, or HbA1c levels) to a control, wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

The disclosure is illustrated by the following non-limiting Examples.

EXAMPLES

Prior studies have suffered from challenges in uncovering metformin's molecular target. Due to its small size, tagging strategies of the drug can be hindered by significant steric effects; for example, in the paper identifying HGB1, the tag used for enrichment of protein/metformin complexes is 3.5 times larger than metformin itself. In addition, the bioavailability of metformin in human liver ranges from 1-5 µM. In order to elicit a significant binding response, the papers identifying complex 1 and required treatment in the mM range, three orders of magnitude higher than the clinically relevant level. The identification of GPD2 and AMP-activated protein kinase required high micromolar levels two orders of magnitude greater than what is physiologically relevant.

In response to these challenges, metformin's binding partner was identified by employing a non-labelling technique that was responsive in the range of the physiological dosing from highly complex enrichments of various cellular compartments, including insoluble membrane proteins, while maintaining native complexes. Differential mass spectrometry, a highly sensitive and reproducible label free quantification and identification strategy, and differential detergent solubilization were employed. By solubilizing isolated membrane proteins and membrane complexes in the presence of metformin, metformin's ability to inhibit membrane localization and insertion can be measured, as proteins and complexes are slower to join the detergent micelles required for solubilization. Centrifugation removes the insolubilized form, and mass spectrometric of metformin versus vehicle treated samples reveal the targets of metformin. In short, ligand binding changes conformation and energy state of the subsequent ligand/protein complex, and detergent solubilization of said complex is slower than the protein alone.

The examples disclosed herein screened over 1,250 membrane proteins, using physiologically relevant dosages of metformin. At both the 5 and 20 µM levels, the top three hits all came from a single protein complex, complex IV. At the 20 µM level, the top 8 scoring proteins are members of complex IV. Additional treatments at 100 µM showed appropriate stronger dosage response. Not to be bound by theory, metformin can act by not allowing complex IV to join the inner mitochondrial membrane, thereby limiting its ability to access the electron potential across the membrane and lowering overall electron chain efficiency, leading to metformin's clinical impact upon metabolic disease.

Example 1

Mass Spectrometry Assay Optimization

Initial experiments were designed to employ the ATP inhibitor staurosporine. Staurosporine is well documented as binding several different kinases, and so offers an a priori known binding event for study and method workup. The workflow for CETSA was streamlined. These improvements are based on two advantages: the use of factory made long heated columns for excellent chromatographic, and therefore sample to sample reproducibility, and the cloud computing platform, Chorus, which allows for the alignment and quantification of hundreds of thousands of mass spectrometric signals without the need to first identify said signals, see U.S. Pat. No. 6,906,320 "Mass Spectrometry Data Analysis Techniques," incorporated herein by reference.

In the staurosporine analysis, the dMS workflow detected 270,822 features that were associated with 108,594 isotope groups. Of these, 23,211 features were annotated with 4,394 peptide sequences from 703 protein sequences. An important and distinguishing feature of the dMS workflow is that results are ranked on the basis of the quantitative data, and significant features may then be identified directly by reanalysis of the sample and acquisition of a MS2 spectrum with a retention time and m/z that matches the features of interest. This quantify first, identify second strategy greatly enhances the depth and precision of proteomic analysis compared to workflows that emphasize peptide identification rates. Features that exhibit a statistically significant difference in relative abundance between the treated and untreated samples were ranked using a combination of statistical and practical filtering. First, 200,256 features that had a non-zero intensity values in a minimum of 6 samples per condition were selected.

Next, a two tailed unpaired equal variance student's t-test was applied, and the fold change between drug treated and vehicle samples calculated. Of these, 140 and 15 significant features belonged to isotope groups with 2 or more significant features having $p<0.01$ and $p<0.0001$, respectively. Next, a targeted nanoLC-MS/MS analysis was used to acquire tandem mass spectra for the 15 highly significant features that resulted in the identification of four peptides from cyclin-dependent kinase 2, CDK2, two peptides from glycogen synthase kinase alpha subunit, GSKA3, and one peptide from Huntingtin-interacting protein K, HYPK. 16 features were found at a significance lower than $p<0.0001$, 1 of these features was unidentified, 2 belonged to HYPK, a non-kinase, and 13 out of 16 belonged to kinases as expected. Also of importance is that no other non-significant peptides were found for these proteins; all the signals from them are significant. This is a high level of precision and ranking ability unique in all thermal shift related workflows.

Initially and attempt was made to find metformin targets in the soluble fractions using this protocol. Although several proteins were implicated, such as catalase, glyceraldehyde phosphate dehydrogenase and others appeared with significant features, the number of insignificant features for these proteins were far greater, leading to the realization that percent significance coverage of a protein was a crucial step in elucidating signal from noise.

Thus, it was recognized that to discover the target of metformin, a generally applicable method was needed to access a wide swath of insoluble proteins and a novel methodology to differentiate between binding and non-binding events. Due to its importance in glucose processing, it was believed that the target of metformin would be found in the liver, and specifically in the mitochondria, necessitating the employment of detergents for the solubilization of these proteins, while not interfering with drug/protein interactions.

Thus, several different detergents were interrogated to find a detergent that met multiple criteria:
1. The detergent must maintain native state
2. The detergent must not interfere with protein ligand binding
3. The detergent must be mass spec compatible
4. The detergent must not interfere with protein/protein binding in existing complexes.

The first criteria excluded several detergents commonly used in mass spectrometry, such as sodium dodecyl sulfate and sodium lithium sulfate. The second criteria is more nebulous, as experiments would have to differentiate between binding/non-binding events. The third criteria is oft overlooked but crucial for establishing a truly industrialized workflow; many detergents used to great success for protein solubilization such as TRITON X-100®, TWEEN®-20, TWEEN®-80, NP-40, and digitonin are not mass spec compatible, nor are they dialyzable prior to mass spec analysis. Only octylglucyl pyranoside (OG) and dodecyl maltoside (DDM) matched all criteria.

Initial experiments were performed on saxagliptin, an anti-diabetic drug that has the known target of DPP4, which is membrane bound in the liver. Samples were homogenized and treated with 1 µM saxagliptin in the presence of 2 CMC of OG to solubilize membrane proteins. Samples were analyzed using a label-free differential mass spectrometry methodology. The method was able to successfully identify DPP4 as showing significantly altered protein intensity in the presence of saxagliptin than with only vehicle. Further validating was that the strongest shift was from another member of the DPP4 family, DPP10, which is not active due to a missing serine-residue in its binding pocket which removes its exopeptidase activity.

Interestingly, the experiment was performed at 37, 41, and 45° C.; the CETSA method dictates that the amount of protein in each subsequent higher temperature should be lower due to thermal stabilization. This was not the case, and the treated samples were the same intensity, regardless of temperature, than the untreated for DPP4.

A critical feature of the CETSA methodology (see U.S. Patent Application 20150133336, incorporated herein by reference) is the use of heat to alter the stability of the protein. The findings demonstrated that the use of detergents, not heat, could be useful and important to study drug/protein binding interactions. In addition, several manuscripts describe that using a protein binding ligand throughout all stages of protein purification yields significantly different protein purification results for x-ray crystallography (Deller, M. C., L. Kong, and B. Rupp, 2016. 72(Pt 2): p. 72-95; Kang, H. J., C. Lee, and D. Int J Biochem Cell Biol, 2013. 45(3): p. 636-44).

The protocol was designed such that membranes were solubilized in the presence of metformin. Thus, membranes from mitochondria, the plasma membrane, peroxisomes, and endoplasmic reticulum would be solubilized in the presence of metformin, to achieve a differential solubilization only for those proteins that interacted with metformin.

The metformin experiment employed several different methodologies to disrupt membranes. Liver tissue was homogenized in a hypotonic buffer and allowed to swell; plasma membranes were disrupted through dounce homogenization. Endoplasmic reticulum (ER), mitochondrial, and peroxisomal membranes were disrupted through bead beating and sonication. Soluble protein lysate was separated from the insoluble fraction with centrifugation. Membranes were split equally and solubilized in OG detergent with and without 5 µM metformin. The experiment was performed with six technical replicates of metformin and vehicle, respectively. Solubilization was allowed to occur at room temperature for 45 minutes with light vortexing followed by 15 minutes without vortexing. Detergent was removed via filter aided dialysis prior to digestion and mass spec analysis.

Chorus analysis identified three proteins as being significantly differentially expressed in metformin as compared to vehicle; COX4i1, COX6b1, and COX5a, as shown in FIG. 1. In FIG. 2, the coverage from the experiment across the proteins for COX4i1, COX6b1, and COX5a; although the method identified several other proteins as highly significant (p<0.0001), a far greater majority of insignificant peptides were found for Hpx and VDAC2. All peptides for COX4i1, COX6b1, and COX5a are very significant (p<0.01). They are the only proteins in the experiment for this to be true; all three are members of Complex IV of the electron transport chain, responsible for the oxidation of reduced ferrocytochrome c. An ADP/ATP binding site on the matrix side of COX4i1 can act as a switch turning on and off complex IV activity based on ATP/ADP ratio. Thus, studies were focused on COX4i1. However, screening methods are designed to assay a functional Complex IV.

Example 2

Materials and Methods

Sample Preparation:

Perfused mouse livers were acquired from Rockland immunochemical. Approximately 100 mg portions of liver were dissected on ice and homogenized for 20 strokes in a glass dounce homogenizer in a hypotonic buffer of 1.5 mM MgCl, 10 mM KCl, and 10 mM HEPES as well as protein inhibitor (Roche). Following 10 minutes of incubation on ice, cells were lysed with 20 additional strokes. Additional homogenization was performed with a MP Biomedicals Fast-prep 24 bead mill homogenizer using lysing matrix A set to 4.5 m/s for 30 seconds as well as a probe sonicator set to 100 watts for 6 cycles of 3 seconds sonication followed by 3 seconds rest on ice. Samples were centrifuged in 100 µl aliquots at 25,000×g for 30 minutes. Soluble lysates were pipetted off and discarded, and insoluble membranes rinsed twice with hypotonic buffer. Samples were incubated for 15 minutes with slight mixing at room temperature in 5, 20, and 100 µM metformin in 0.05% DMSO (n=6 per treatment or control) or 0.05% DMSO alone, in a buffer of 10 mM MgCl, 50 mM KCl, and 40 mM HEPES with protease inhibitors. After incubation, octyl-glucoside was added to a final concentration of 2 CMC and incubated for an additional 15 minutes. After incubation, insolubilized materials were removed by centrifugation at 25,000×g for 30 minutes.

30 µg of now solubilized membrane proteins was digested per sample using the FASP method (Wisniewski, J. R., A. Zougman, N. Nagaraj and M. Mann (2009). Nat Methods 6(5): 359-362) with minor modifications. Samples were added to 200 µl of 100 mM Tris-HCl, pH 8.0, 8M urea in an YM30 Microcon microcentrifuge filter (Millipore, Darmstadt, DEU). Samples were centrifuged for 15 minutes at 14,000 g before an additional 200 µl of urea buffer was added and centrifugation repeated. 100 µl of 100 mM Tris-HCl, pH 8.0, 20 mM iodoacetamide, 8M urea was added and samples incubated in the dark at room temperature for 20 minutes before centrifugation at the settings above. Three 100 µl volumes of urea buffer were added and centrifuged between additions at 14,000 g for 14, 13, and 12 minutes, respectively. Three 100 µl volumes of 50 mM ammonium bicarbonate were added and centrifuged between additions for 12, 12, and 10 minutes, respectively. 100 µl of 50 mM ammonium bicarbonate with Sequence Grade TPCK-Treated Trypsin (Promega, Fitchburg, Wis.) were added to the samples in a ratio of 50 to 1 protein to trypsin by mass and the samples digested overnight in a humidified 37° C. incubator. Peptides were recovered into a new tube using two elutions of 100 μl of 50 mM ammonium bicarbonate recovered via centrifugation at 14,000×g for 10 and 15 minutes, respectively.

Samples were desalted on a vacuum manifold using 50 mg bed reversed-phase C18 solid phase columns (Supelco, Bellefonte, Pa.) as described previously. Briefly, columns were activated with 0.1% formic acid in acetonitrile, followed by equilibration with 0.1% formic acid in water. Following loading, samples were washed with 0.1% formic acid in water. Samples were eluted in 90% acetonitrile, 1% water 0.1% formic acid. Samples were dried down in a Centrivap Concentrator with in-line cold trap (Labconco, Kansas City, Mo.) prior to resuspension in 0.1% formic acid in water at a concentration of 3 μg/μl.

LC Separation and Mass Spectrometric Analysis:

Samples were loaded in a NanoAcquity UPLC autosampler (Waters, Milford, Mass.) maintained at 4° C. A 1 μL aliquot of sample was directly injected using a flow rate of 300 nl/min onto a modular Picochip XL electrospray ionization chip (New Objective, Cambridge, Mass.) heated to 50° C. equipped with a 25 cm, 75 micron ID fused silica column filled with 1.9 μm reversed phased C-18 REPROSIL with 300 angstrom pore size (Dr. Maisch, DEU). Loaded samples were washed for 8 minutes in 3% acetonitrile in water and 0.1% formic acid prior to a 60 minute gradient to 32%. Flow was increased to 80% acetonitrile in 2 minutes and held for 8 minutes before a fifteen minute wash at 3% acetonitrile.

High resolution mass spectrometry data was acquired with a hybrid orbital ion trap mass spectrometer ORBItrap XL for the 5 μM treatments and an ORBItrap Velos Pro for the 20 and 100 μM (Thermo Fischer Scientific, Waltham, Mass.). Full scan spectra were acquired with a resolving power setting of 60,000. Tandem mass spectra were acquired using a data dependent acquisition method that collects 4 MS/MS spectra in the instruments linear ion trap mass analyzer. Automatic Gain Control target settings of 106 and 5×103 ions were used for full and dependent spectra, respectively, with a maximum fill time of 150 ms for dependent spectra. An exclusion list setting of 500 items was employed with a delay of 60 seconds. Data dependent acquisitions settings were adjusted to exclude singly charges species and ions without an assigned charge state.

Feature Quantification and Identification:

A label free differential mass spectrometry workflow was used for analysis and quantification of the high resolution LC-MS data. Native instrument files were translated from the vendor specific format (*.RAW) and converted to a vendor neutral format prior to analysis. Quantitative analysis aligned and quantified mass spectrometric signals, referred to here as "features", as defined by their accurate mass/charge ratio, retention time, and relative intensity. Translated files are first processed as a two dimensional image with axes of accurate mass/charge and retention time, with the point size defined by relative intensity. Features are then clustered into isotope groups. A datacube is created by aligning the features by retention time across all sample images. MS/MS data and high resolution full scan precursor masses were searched using Comet against the Uniprot reference set for *Mus musculus*. Full scan mass tolerance was set to 20 ppm and 0.8 Daltons for MS/MS scans, and two missed cleavages were allowed.

Protein intensities were calculated by taking the median intensity for all peptides associated with that protein. A Student's unpaired equal variance t-test was performed across all samples to establish statistical significance.

Example 3

Identifying Targets of Metformin at Physiological Doses

Initial 5 μM treatments successfully quantified 490 proteins across 1405 peptides in at least 5 of 6 samples per treatment group. Upon statistical significance testing at the peptide level, the top 3 most significantly different proteins were members of complex IV; cytochrome c oxidase subunit 4 isoform 1 (COX4I1), cytochrome c oxidase subunit 5A (COX5A), and cytochrome c oxidase subunit 6b1 (COX6B1). COX4I1 was quantified at 2.5 times lower in metformin treatment than vehicle with a p-value of $1.6 \times 10^{-6}$. COX5A was quantified at 2.4 times lower in metformin treatment than vehicle with a p-value of $5.8 \times 10^{1'}$. COX6B1 was quantified at 3.0 times lower in metformin treatment than vehicle with a p-value of $7.6 \times 10^{-8}$. No other proteins from complex IV were found in the analysis. Volcano and box plots of the analysis can be found in FIG. 3.

Additional treatments were performed at 20 and 100 μM. 1259 proteins and 8,851 peptides were quantified. At both levels, 9 of 13 members of complex IV were found. Of these, 6 of 9 had greater significance than any other protein and all had lower negative fold changes than all other proteins, as shown in FIG. 4.

Figure 5:
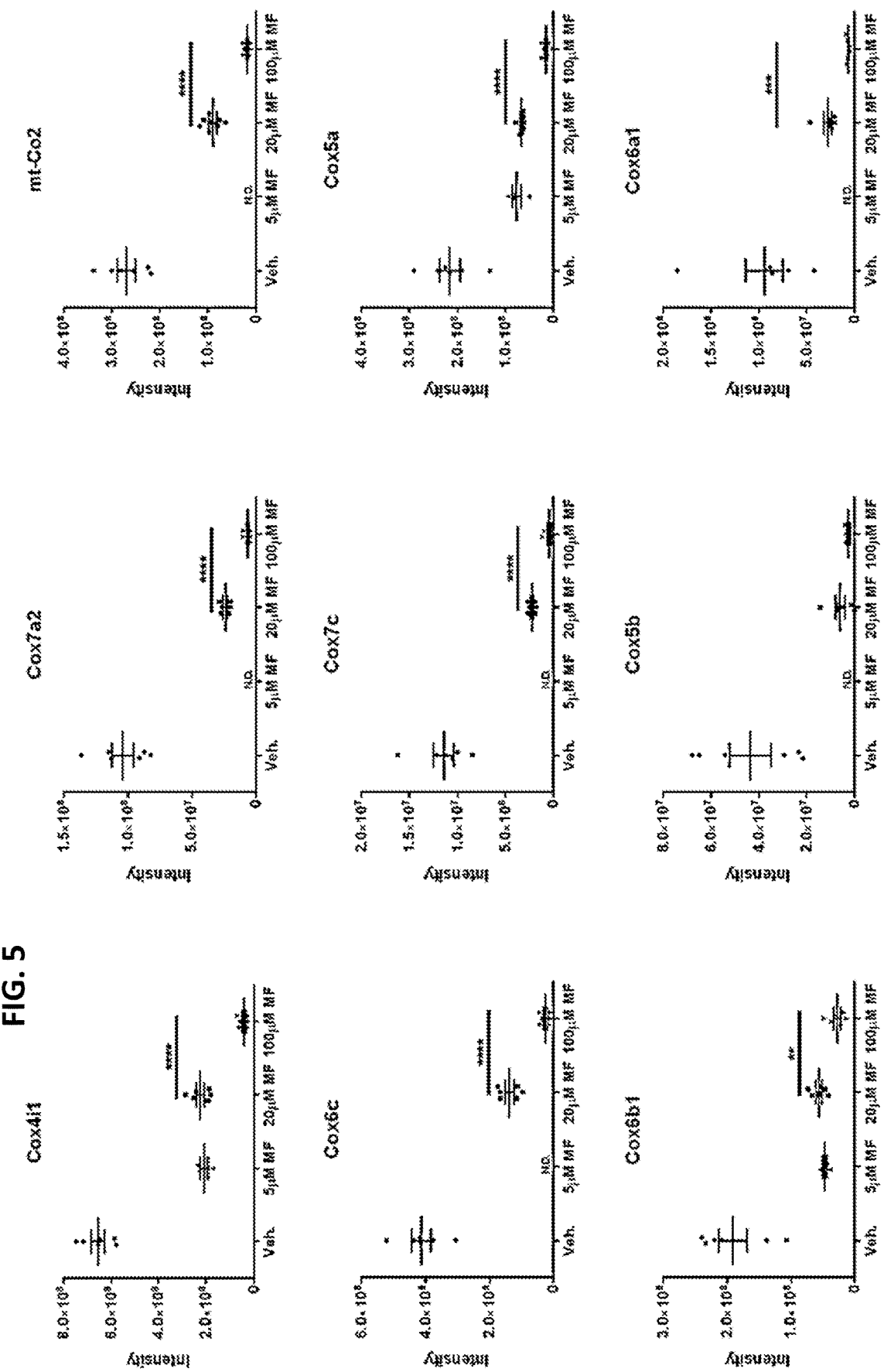
FIG. 5: Differential solubilization of membrane proteins across all treatment levels for dose dependence analysis. Scattered dot plots for each protein is shown as mean and SEM and individual protein levels. Statistical analysis between 20 μM and 100 μM via Student's unpaired equal variance t-test. **, $p<0.0001$; *, $p<0.001$; **, $p<0.01$.

Dose dependence analysis comparing the 5, 20, and 100 μM was performed. For the three proteins found in experiments with 5, 20, and 100 no significant differences were found between the 5 and 20 μM, however significant differences were found for 8 of 9 proteins between the 20 and 100 μM treatments, as shown in FIG. 5, with the 100 μM treatment having on average a 3 fold decrease in complex solubilization.

Using a label-free differential mass spectrometry approach and differential detergent solubilization, it was determined that the proteins of complex IV of the mitochondrial electron transport chain have significantly lower solubility if first treated with metformin prior to detergent solubilization. The effect is durable across multiple reproductions and shows expected dose dependence. In addition, the dosage required to cause the binding effect is within the clinically relevant range, greatly increasing the impact of the finding.

In addition, the effect is reproducible across all proteins of the complex at similar levels of effect, implying that the complex is solubilized intact and the entire complex is affected by metformin. Without access to the electron gradient across the inner mitochondrial membrane, complex IV will not be able to function, hampering electron transport chain activity. This alteration in function may be causing the metabolic effects of metformin.

In view of the many possible embodiments to which the principles of the disclosure may be applied, it should be recognized that the illustrated embodiments are only preferred examples of the disclosure and should not be taken as limiting the scope of the disclosure. Rather, the scope of the disclosure is defined by the following claims. We therefore claim all that comes within the scope and spirit of these claims.

We claim:

1. A method for identifying a compound of use in treating a condition treatable by metformin, comprising:
   contacting a sample comprising a mitochondrial electron transport complex IV with a test compound; and
   determining if the test compound binds a subunit of the mitochondrial electron transport complex IV, wherein the subunit is Cox4i1, Cox5a, Cox6b1, Cox7a2, mt-Co2, Cox6c, Cox7c, Cox5b, or Cox6a1, and
   wherein binding of the test compound to the subunit or change in function of the mitochondrial electron transport complex IV, indicates that the compound is of use in treating the condition.

2. The method of claim 1, wherein the subunit of the mitochondrial electron transport complex IV is Cox4i1.

3. The method of claim 2, wherein the test compound binds an ADP/ATP binding site on a matrix side of the COX4i1.

4. The method of claim 1, wherein the condition is type II diabetes.

5. A method for identifying a compound of use in treating a condition treatable by metformin, comprising:
   contacting a sample comprising a mitochondrial electron transport complex IV with a test compound; and
   determining if the test compound binds a subunit of mitochondrial electron transport complex IV;
   wherein determining if the test compound binds the subunit of the mitochondrial electron transport complex IV comprises performing mass spectrometry, and
   wherein binding of the test compound to the mitochondrial electron transport complex IV indicates that the compound is of use in treating the condition.

6. The method of claim 5, wherein mass spectrometry is differential mass spectrometry.

7. The method of claim 5, further comprising contacting the sample with an effective amount of Octyl β-d-glucopyranoside prior to performing the mass spectrometry.

8. The method of claim 1, wherein the method is a competitive binding assay.

9. The method of claim 8, wherein the competitive binding assay comprises the use of metformin.

10. The method of claim 1, wherein the sample is a liposome comprising the mitochondrial electron transport complex IV.

11. The method of claim 8, wherein:
    the sample is a liposome comprising the mitochondrial electron transport complex IV; and
    the assay comprises:
    contacting the liposome with labelled ADP and/or labelled ATP and the test compound; and
    measuring binding of the labelled ADP and/or labelled ATP to the mitochondrial electron transport complex IV.

* * * * *